United States Patent
Perryman et al.

(10) Patent No.: US 9,446,251 B1
(45) Date of Patent: Sep. 20, 2016

(54) HANDHELD TREATMENT DEVICE

(71) Applicant: Micron Devices LLC, Miami Beach, FL (US)

(72) Inventors: Laura Tyler Perryman, Miami Beach, FL (US); Graham Patrick Greene, Miami Beach, FL (US); Chad David Andresen, Miami Beach, FL (US)

(73) Assignee: Micron Devices LLC, Miami Beach, FL (US)

( * ) Notice: Subject to any disclaimer, the term of this patent is extended or adjusted under 35 U.S.C. 154(b) by 0 days.

(21) Appl. No.: 14/615,360

(22) Filed: Feb. 5, 2015

Related U.S. Application Data

(60) Provisional application No. 61/936,191, filed on Feb. 5, 2014.

(51) Int. Cl.
*A61N 1/36* (2006.01)
*A61N 1/372* (2006.01)
*A61N 1/378* (2006.01)

(52) U.S. Cl.
CPC ....... *A61N 1/37229* (2013.01); *A61N 1/36128* (2013.01); *A61N 1/3787* (2013.01); *A61N 1/37247* (2013.01)

(58) Field of Classification Search
CPC .......... A61N 1/37229; A61N 1/3787; A61N 1/37223
See application file for complete search history.

(56) References Cited

U.S. PATENT DOCUMENTS

| | | | | |
|---|---|---|---|---|
| 4,361,153 | A * | 11/1982 | Slocum | A61B 5/0017 128/903 |
| 6,275,737 | B1 * | 8/2001 | Mann | A61N 1/08 607/61 |
| 9,030,159 | B2 * | 5/2015 | Chen | A61N 1/3787 320/108 |
| 2005/0075692 | A1 * | 4/2005 | Schommer | A61N 1/37229 607/60 |
| 2010/0204756 | A1 * | 8/2010 | Aghassian | A61N 1/37223 607/60 |
| 2012/0326886 | A1 * | 12/2012 | Herman | A61N 1/37229 340/870.07 |

* cited by examiner

*Primary Examiner* — George Evanisko
(74) *Attorney, Agent, or Firm* — Fish & Richardson P.C.

(57) ABSTRACT

A handheld treatment device can include a handheld housing; a transmitting antenna located in the handheld housing and configured to accept one or more input signals and to transmit one or more electromagnetic signals to a neural stimulator that is implanted in the patient's body; and control circuitry located in the handheld housing and configured to provide the one or more input signals to the transmitting antenna.

16 Claims, 29 Drawing Sheets

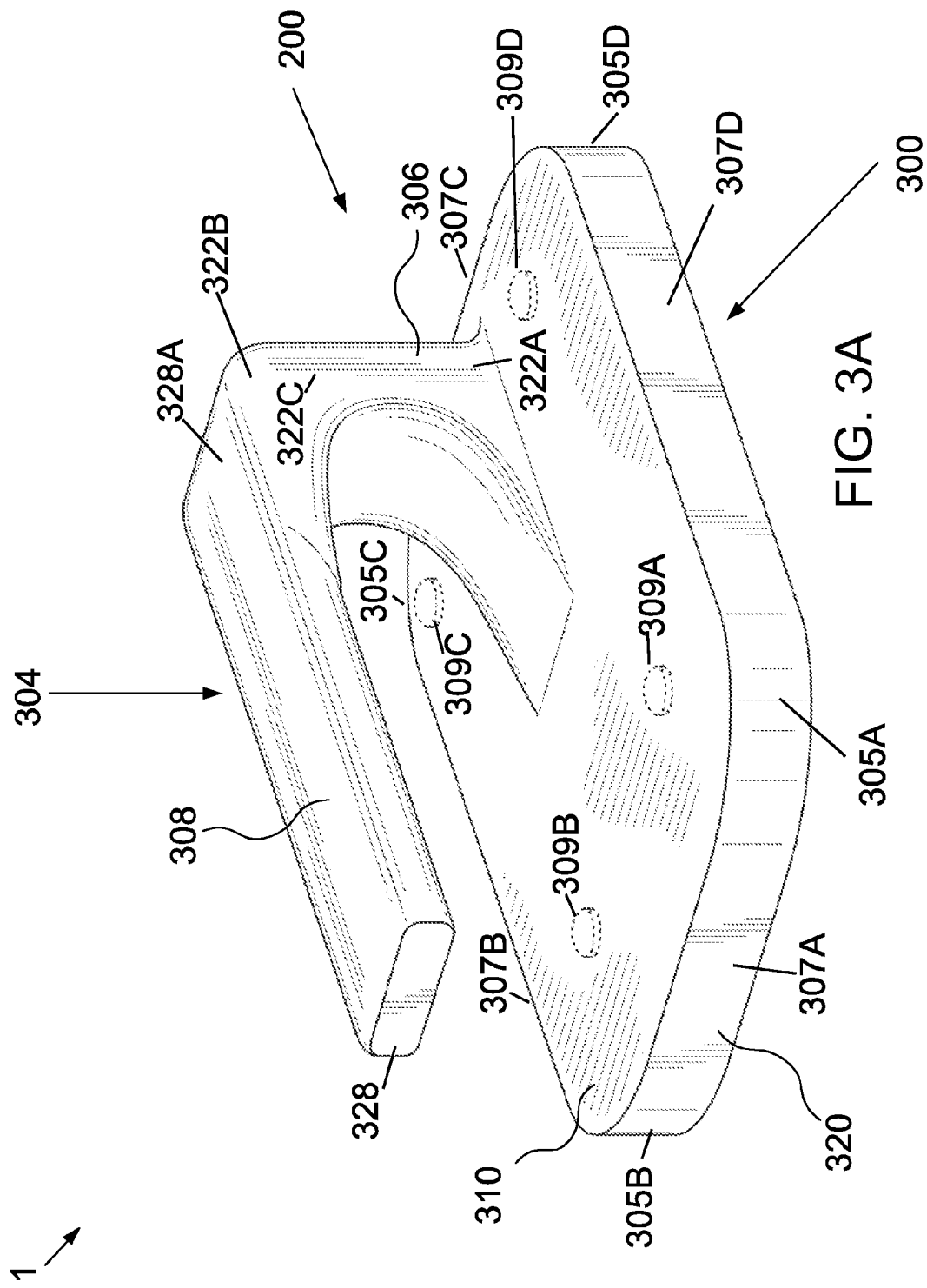

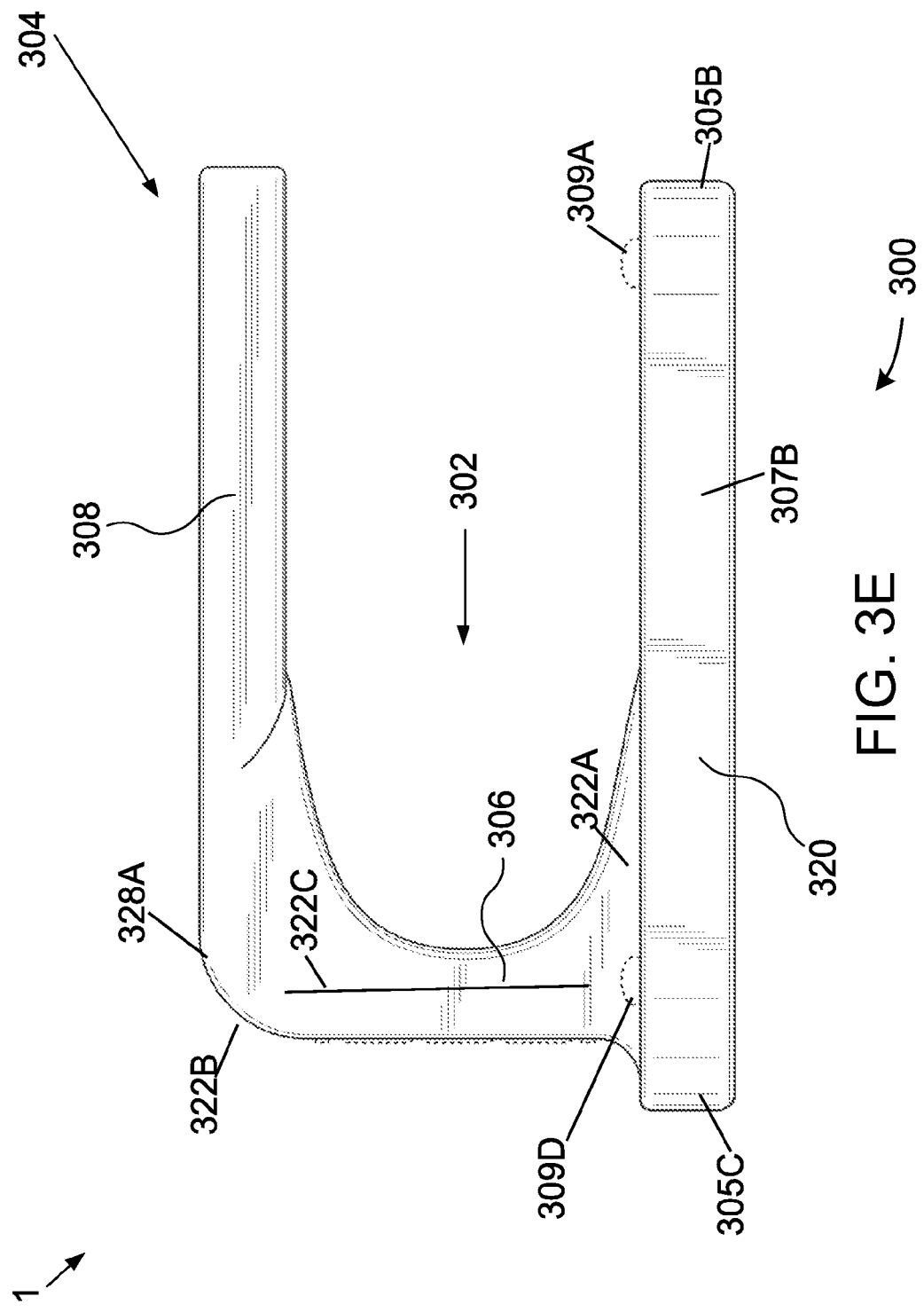

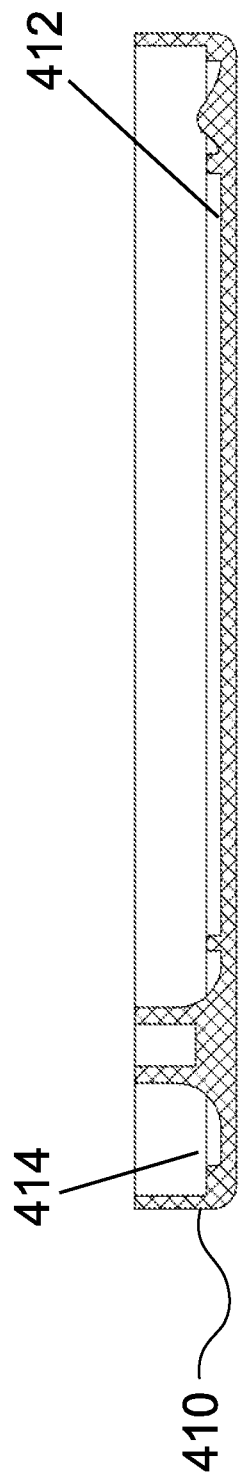
FIG. 4B
FIG. 4C

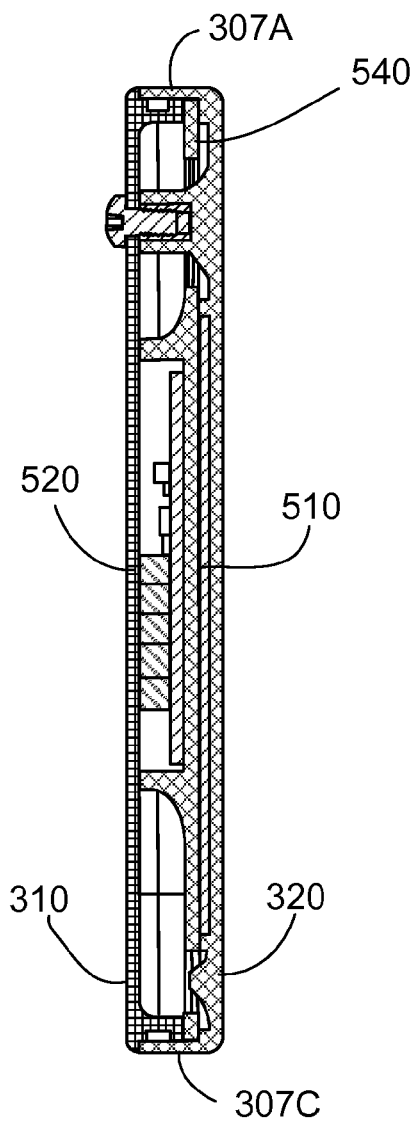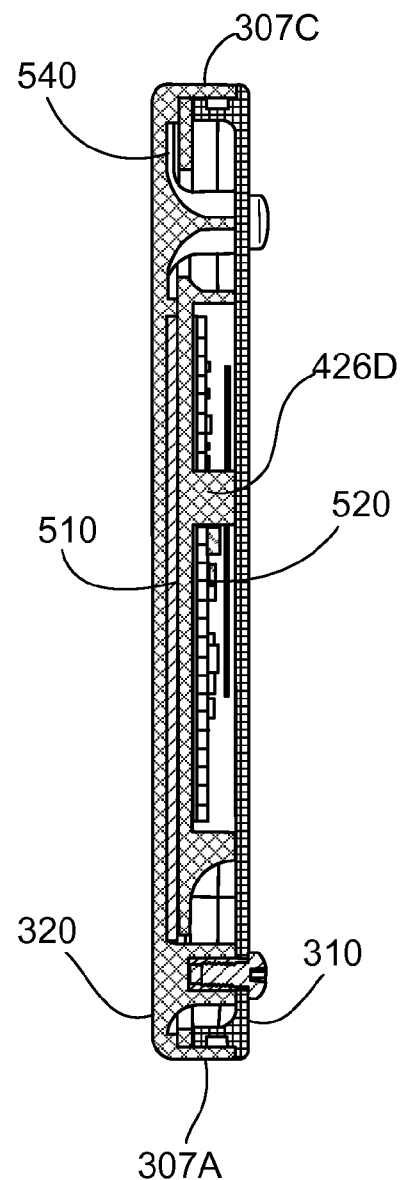
FIG. 8B
FIG. 8C

HANDHELD TREATMENT DEVICE

CROSS REFERENCE TO RELATED APPLICATIONS

This application claims the benefit of priority of U.S. Provisional Patent Application No. 61/936,191, filed Feb. 5, 2014, the complete disclosure of which is hereby incorporated by reference in entirety for all purposes.

BACKGROUND

Modulation of neural tissue in the body by electrical stimulation has become an important type of therapy for chronic disabling conditions, such as chronic pain, problems of movement initiation and control, involuntary movements, dystonia, urinary and fecal incontinence, sexual difficulties, vascular insufficiency, heart arrhythmia, and more. Electrical stimulation of the spinal column and nerve bundles leaving the spinal cord was the first approved neural modulation therapy and has been used commercially since the 1970s. Implanted electrodes are used to pass pulsatile electrical currents of controllable frequency, pulse width, and amplitudes. Two or more electrodes are normally in contact with neural elements, chiefly axons, and can selectively activate varying diameters of axons, with positive therapeutic benefits. A variety of therapeutic intra-body electrical stimulation techniques are utilized to treat neuropathic conditions that utilize an implanted neural stimulator in the spinal column or surrounding areas, including the dorsal horn, dorsal root ganglia, dorsal roots, dorsal column fibers, and peripheral nerve bundles leaving the dorsal column or brain, such as vagus-, occipital-, trigeminal-, hypoglossal-, sacral-, and coccygeal nerves.

SUMMARY

In one aspect, some implementations provide a handheld treatment device for facilitating neurophysiological treatment of a patient harboring an implanted neural stimulator, the handheld treatment device including: a handheld housing; a transmitting antenna located in the handheld housing and configured to accept one or more input signals and to transmit one or more electromagnetic signals to a neural stimulator that is implanted in the patient's body; control circuitry located in the handheld housing and configured to provide the one or more input signals to the transmitting antenna.

Implementations may include one or more of the following features. The handheld housing may include a bottom portion having a bottom surface connected to a top portion having a handle member adapted for holding by a hand of an operator. The transmitting antenna may be located in the bottom portion; and the control circuitry may be located in the bottom portion. The transmitting antenna may be a patch antenna, a dipole antenna, spiral antenna or other antenna configuration within a form factor of the handheld treatment device.

The handheld treatment device may further include an inductive charging component for transferring electrical energy to a battery mounted in the bottom portion of the handheld treatment device.

The handheld treatment device may additionally include a control panel with at least one interface button. The control panel may be located on a surface of the top portion of the handheld treatment device. The control panel may be connected to the control circuitry by a cable, and the cable may pass through a hollow portion of the top portion of the handheld treatment device. The first interface button of the at least one interface button may control at least one neuro stimulation setting of the control circuitry. The at least one neural stimulation setting may include at least one of: an amplitude setting, a pulse width setting, a frequency setting, and a preset programs setting. A second interface button of the at least one interface button may control which neural stimulation setting of the at least one neural stimulation setting is controlled by the first interface button.

An elongate portion of the handle member may be substantially parallel to the bottom surface of the bottom portion. A primary transmission surface of the transmitting antenna may be substantially parallel to the bottom surface of the bottom portion. The bottom surface of the bottom portion may be located between the primary transmission surface of the transmitting antenna and the implanted neural stimulator.

The handheld treatment device may further include a battery located in the bottom portion, which provides electrical power to at least the control circuitry. The handheld treatment device may further include at least one charging coil to recharge the battery. The recharging coil may be configured to receive energy wirelessly from a source external to handheld treatment device and use the energy to recharge the battery.

The bottom portion may include a base housing section segment that defines the bottom surface and, on a surface opposite the bottom surface, defines an antenna recess in which the transmitting antenna is located; an antenna cover housing section that is arranged in the base housing section such that a first surface of the antenna cover housing is facing the transmitting antenna in the antenna recess; and wherein the antenna housing section includes a second surface, opposite the first surface of the antenna housing section, that includes a central circuit board and battery space in which a circuit board supporting the control circuitry and a battery are located, the antenna housing section providing electrical isolation between the antenna and the circuit board.

BRIEF DESCRIPTION OF THE DRAWINGS

FIGS. 3A to 3G shows various views of the handheld treatment device of FIG. 1.

FIGS. 4A to 4E show cutaway views and perspective views of the handheld treatment device of FIG. 1.

FIG. 8A to 8G depict various side cutaway views of the handheld treatment device of FIG. 1.

DETAILED DESCRIPTION

In various implementations, a neural stimulation system may include a handheld treatment device and a passive implanted neural stimulator that contains one or more antennas, one or more circuits, and one or more electrodes in contact with or in proximity to targeted neural tissue. The handheld treatment device may include circuitry and an antenna that are configured to transfer energy from the antenna to the implanted neural stimulator. The one or more circuits of the implanted neural stimulator may be configured to extract the transferred energy and use the extracted energy to generate electrical pulses suitable for neural stimulation and to supply the electrical pulses to the electrodes so that the pulses are applied to the neural tissue. The neural stimulation system accordingly may be used to send electrical stimulation to targeted nerve tissue by using electromagnetic energy with neither cables nor inductive coupling to power the passive implanted stimulator. The targeted nerve tissues may be, for example, in the spinal column including the spinothalamic tracts, dorsal horn, dorsal root ganglia, dorsal roots, dorsal column fibers, and peripheral nerves bundles leaving the dorsal column or brainstem, as well as any cranial nerves, abdominal, thoracic, or trigeminal ganglia nerves, nerve bundles of the cerebral cortex, deep brain and any sensory or motor nerves.

Figure 1:
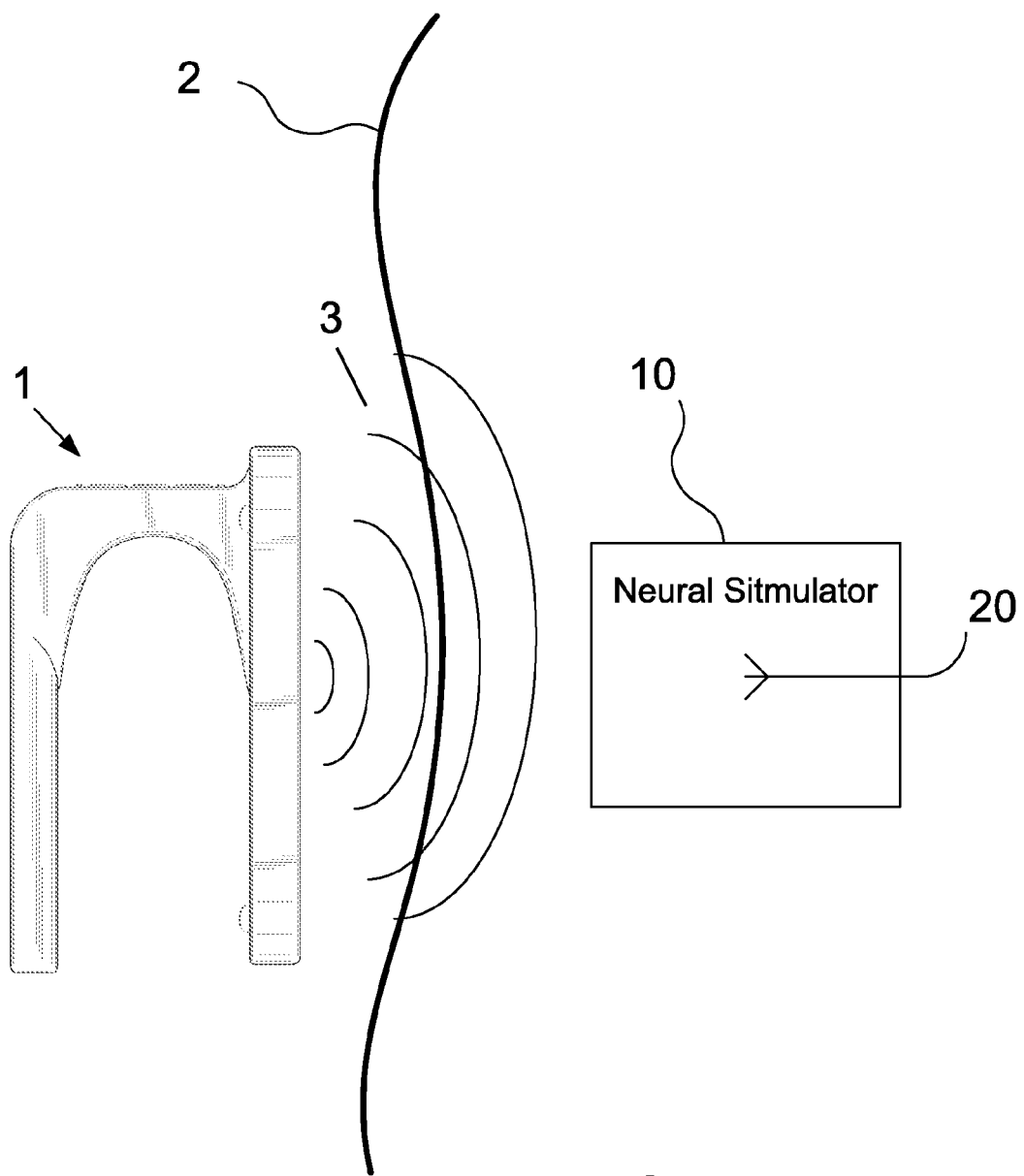
FIG. 1 depicts an example of a handheld treatment device transmitting electromagnetic energy to an implanted neural stimulator.

FIG. 1 depicts an example of a handheld treatment device 1 transmitting electromagnetic energy to power an implanted neural stimulator 10. The handheld treatment device 1 includes an antenna, stimulation circuitry, and a battery. These components are embedded within the packaging form factor of the handheld treatment device 1. The handheld treatment device 1 is external to a patient's body and may be placed in contact with, or close proximity to (for example, within 3 feet) of the patient's skin 2. The stimulation circuitry and antenna of the handheld treatment device 1 are used to transmit electromagnetic signals 3 that power the implanted neural stimulator 10, which does not have its own independent power source. The implanted wireless neural stimulator 10 contains one or more antennas 20, such as dipole antenna(s), to receive the transmitted signals from the handheld treatment device 1.

The coupling mechanism between the antenna of the handheld treatment device 1 and the one or more antennas on the implanted neural stimulator 10 is electrical radiative coupling and not inductive coupling. In some implementations, the transmission signal may employ a modulated carrier signal in the microwave range, for example, from about 300 MHz to about 8 GHz, or more specifically from about 800 MHz to 1.3 GHz. Through this electrical radiative coupling, the antenna of the handheld treatment device 10 can provide an input signal to the implanted neural stimulator 10. This input signal contains energy and may contain information encoding stimulus waveforms to be applied at the electrodes of the implanted neural stimulator 10 to electrically stimulate target neural tissue. In some implementations, the power level of this input signal directly determines an applied amplitude (for example, power, current, or voltage) of the one or more electrical pulses created using the electrical energy contained in the input signal. Within the implanted wireless neural stimulator 10 are components for receiving the input signal, using the input signal to create electrical pulses, and electrodes to deliver the electrical pulses to surrounding neural tissue.

Accordingly, through electrical radiative coupling, handheld treatment device 1 radiates a transmission signal 3 to antenna 20 within the implanted neural stimulator 10. The transmission signal propagates through skin 2 and underlying tissues to arrive at the antenna 20 within the implanted neural stimulator 10. The implanted neural stimulator 10 uses the transmission signal to generate electrical pulses that are applied to target neural tissue.

Figure 2A:
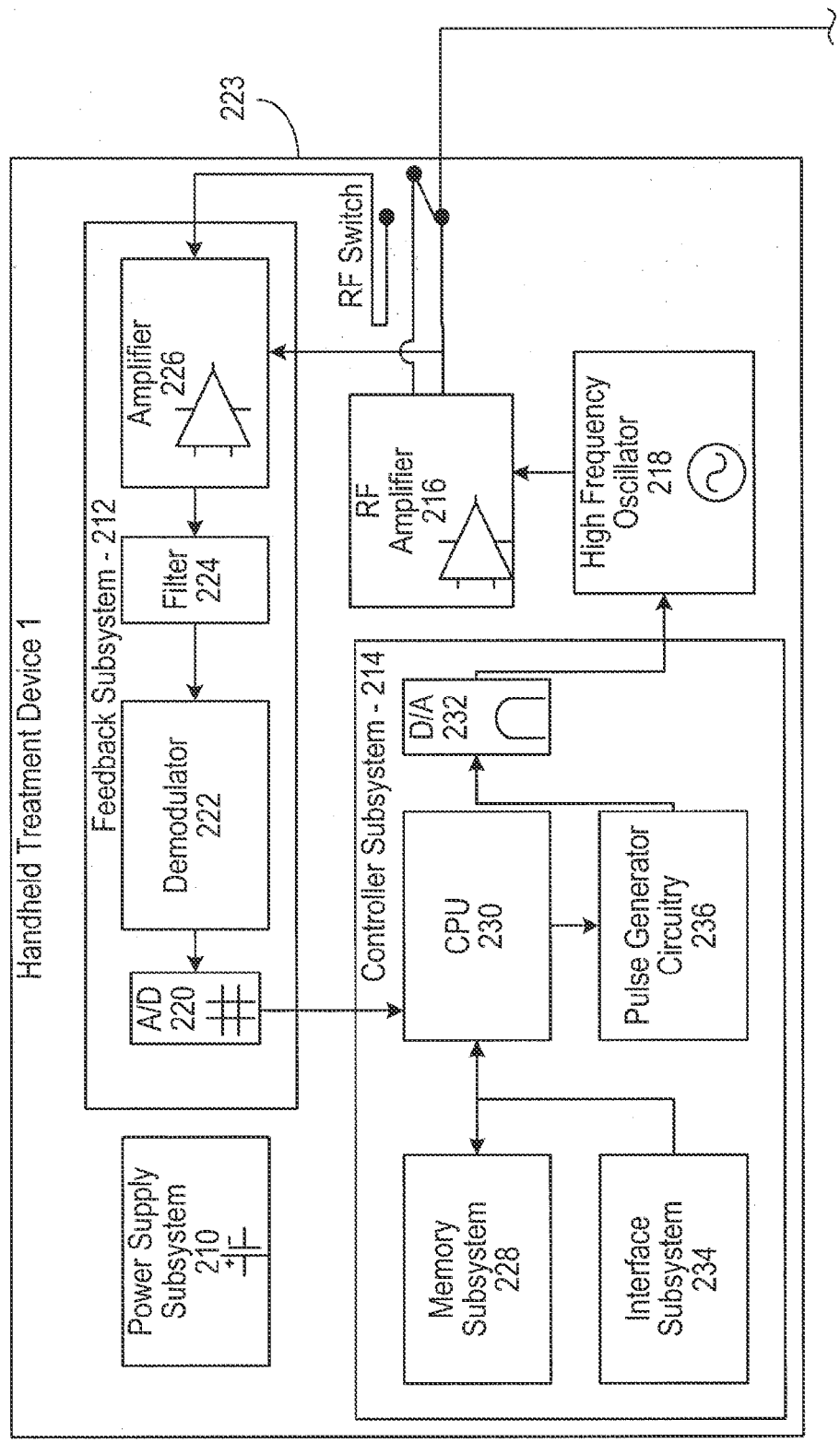
FIGS. 2A and 2B depict a detailed diagram of the handheld treatment device of FIG. 1 interacting with an implanted neural stimulator device.
Figure 2B:
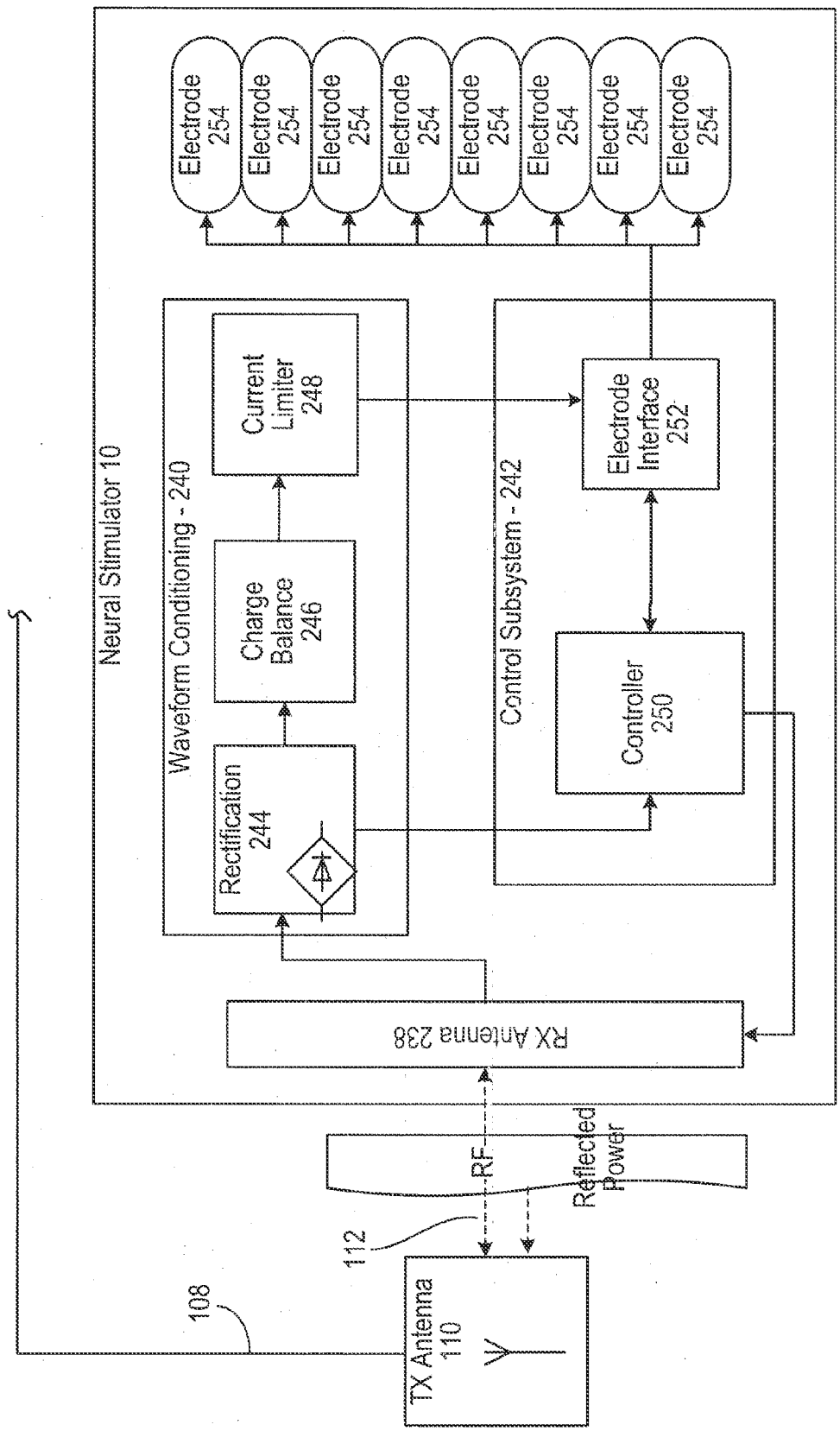

FIGS. 2A and 2B depict a block diagram illustrating an example of electronic components of handheld device 1 and neural stimulator 10. As illustrated, handheld treatment device 1 controls stimulation parameters of implanted neural stimulator 10. The stimulation parameters that can be controlled may include pulse amplitude, pulse frequency, and pulse width in the ranges shown in Table 1. In this context the term pulse refers to the phase of the waveform that directly produces stimulation of the tissue; the parameters of the charge-balancing phase (described below) can similarly be controlled. The patient and/or the clinician can also optionally control overall duration and pattern of treatment.

| Stimulation Parameter Table 1 | |
|---|---|
| Pulse Amplitude: | 0 to 24 mA |
| Pulse Frequency: | 0 to 50,000 Hz |
| Pulse Width: | 0 to 2 ms |

The implantable neural stimulator 10 or handheld treatment device 1 may be initially programmed to meet the specific parameter settings for each individual patient during the initial implantation procedure. Because medical conditions or the body itself can change over time, the ability to re-adjust the parameter settings may be beneficial to ensure ongoing efficacy of the neural modulation therapy. The handheld treatment device 1 includes a transmitting antenna 110.

The signals sent by handheld treatment device 1 to the implanted stimulator 10 may include both power and parameter-setting attributes in regards to stimulus waveform, amplitude, pulse width, and frequency. The handheld treatment device 1 can also function as a wireless receiving unit that receives feedback signals from the implanted neural stimulator 10. To that end, handheld treatment device 1 may contain microelectronics or other circuitry to handle the generation of the signals transmitted to the neural stimulator 10 as well as handle feedback signals, such as those from neural stimulator 10. For example, handheld treatment device 1 may include controller subsystem 214, high-frequency oscillator 218, RF amplifier 216, a RF switch, and a feedback subsystem 212.

The controller subsystem 214 may include a CPU 230 to handle data processing, a memory subsystem 228 such as a local memory, interface subsystem 234 to communicate with a user (including receiving choices of stimulation parameters from the user), pulse generator circuitry 236, and digital/analog (D/A) converters 232.

The controller subsystem 214 may be used by the patient and/or the clinician to control the stimulation parameter settings (for example, by controlling the parameters of the signal sent from handheld treatment device 1 to neural stimulator 10). These parameter settings can affect, for example, the power, current level, or shape of the one or more electrical pulses. Example parameters include repetition rate, pulse width, amplitude, and waveform to be transmitted by RF energy to the receive (RX) antenna 238, for example a dipole antenna (although other types may be used), in the wireless implanted neural stimulator 10.

The controller subsystem 214 may store received parameter settings in the local memory subsystem 228, until the parameter settings are modified by new input data received via the interface subsystem 234. The CPU 206 may use the parameters stored in the local memory to control the pulse generator circuitry 236 to generate a stimulus waveform that is modulated by a high frequency oscillator 218 in the range from 300 MHz to 8 GHz. The resulting RF signal may then be amplified by RF amplifier 226 and then sent through an RF switch 223 to the transmitting antenna 110 to reach through depths of tissue to the implanted antenna 238.

In some implementations, the RF signal sent by transmitting antenna 110 may simply be a power transmission signal used by neural stimulator 10 to generate electric pulses. In other implementations, a program signal may also be transmitted to neural stimulator 10 that includes instructions on the various operations of the implanted neural stimulator 10. In still other implementations, a telemetry signal nay be transmitted from neural stimulator 10 and received at transmitting antenna 110. The telemetry signal may be sent by the modulation of the carrier signal (through the skin if external, or through other body tissues if the handheld treatment device 1 is implanted subcutaneously). The telemetry signal is used to modulate the carrier signal (a high frequency signal) that is coupled onto the implanted antenna(s) 238 and does not interfere with the input received on the same lead to power the implant. In one embodiment the telemetry signal and powering signal are combined into one signal, where the RF telemetry signal is used to modulate the RF powering signal, and thus the implanted stimulator is powered directly by the received telemetry signal; separate subsystems in the stimulator harness the power contained in the signal and interpret the data content of the signal.

The RF switch 223 may be a multipurpose device such as a dual directional coupler, which passes the relatively high amplitude, extremely short duration RF pulse to the transmitting antenna 110 with minimal loss while simultaneously providing two low-level outputs to feedback subsystem 212; one output delivers a forward power signal to the feedback subsystem 212, where the forward power signal is an attenuated version of the RF pulse sent to the transmitting antenna 110, and the other output delivers a reverse power signal to a different port of the feedback subsystem 212, where reverse power is an attenuated version of the reflected RF energy from the transmitting Antenna 110.

During the on-cycle time (when an RF signal is being transmitted to implanted neural stimulator 10), the RF switch 223 is set to send the forward power signal to feedback subsystem. During the off-cycle time (when an RF signal is not being transmitted to the implanted neural stimulator 10), the RF switch 223 can change to a receiving mode in which the reflected RF energy and/or RF signals from the implanted neural stimulator 10 are received to be analyzed in the feedback subsystem 212.

The feedback subsystem 212 of the handheld treatment device 1 may include reception circuitry to receive and extract telemetry or other feedback signals from the neural stimulator 10 and/or reflected RF energy from the signal sent by the transmitting antenna 110. The feedback subsystem may include an amplifier 226, a filter 224, a demodulator 222, and an A/D converter 220.

The feedback subsystem 212 receives the forward power signal and converts this high-frequency AC signal to a DC level that can be sampled and sent to the controller subsystem 214. In this way the characteristics of the generated RF pulse can be compared to a reference signal within the controller subsystem 214. If a disparity (error) exists in any parameter, the controller subsystem 214 can adjust the output to the handheld treatment device 1. The nature of the adjustment can be, for example, proportional to the computed error. The controller subsystem 214 can incorporate additional inputs and limits on its adjustment scheme such as the signal amplitude of the reverse power and any predetermined maximum or minimum values for various pulse parameters.

The reverse power signal can be used to detect fault conditions in the RF-power delivery system. In an ideal condition, the transmitting antenna 110 has perfectly matched impedance to tissue and the electromagnetic waves generated from the handheld treatment device 1 pass unimpeded from the transmitting antenna 110 into the body tissue. However, in real-world applications a large degree of variability may exist in the body types of users, types of clothing worn, and positioning of the antenna 110 relative to the body surface. Since the impedance of the antenna 110 depends on the relative permittivity of the underlying tissue and any intervening materials, and also depends on the overall separation distance of the antenna from the skin, in any given application there can be an impedance mismatch at the interface of the transmitting antenna 110 with the body surface. When such a mismatch occurs, the electromagnetic waves sent from the handheld treatment device 1 are partially reflected at this interface, and this reflected energy propagates backward through the antenna feed.

The dual directional coupler RF switch 223 may prevent the reflected RF energy propagating back into the amplifier 226, and may attenuate this reflected RF signal and send the attenuated signal as the reverse power signal to the feedback subsystem 212. The feedback subsystem 212 can convert this high-frequency AC signal to a DC level that can be sampled and sent to the controller subsystem 214. The controller subsystem 214 can then calculate the ratio of the amplitude of the reverse power signal to the amplitude of the forward power signal. The ratio of the amplitude of reverse power signal to the amplitude level of forward power may indicate severity of the impedance mismatch.

In order to sense impedance mismatch conditions, the controller subsystem 214 can measure the reflected-power ratio in real time, and according to preset thresholds for this measurement, the controller subsystem 214 can modify the level of RF power generated by the handheld treatment device 1. For example, for a moderate degree of reflected power the course of action can be for the controller subsystem 214 to increase the amplitude of RF power sent to the transmitting antenna 110, as would be needed to compensate for slightly non-optimum but acceptable transmitting antenna coupling to the body. For higher ratios of reflected power, the course of action can be to prevent operation of the handheld treatment device 1 and set a fault code to indicate that the transmitting antenna 110 has little or no coupling with the body. This type of reflected-power fault condition can also be generated by a poor or broken connection to the transmitting antenna. In either case, it may be desirable to stop RF transmission when the reflected-power ratio is above a defined threshold, because internally reflected power can lead to unwanted heating of internal components, and this fault condition means the system cannot deliver sufficient power to the implanted neural stimulator and thus cannot deliver therapy to the user.

The controller 242 of the implanted neural stimulator 10 may transmit informational signals, such as a telemetry signal, through the antenna 238 to communicate with the handheld treatment device 1 during its receive cycle. For example, the telemetry signal from the neural stimulator 10 may be coupled to the modulated signal on the dipole antenna(s) 238, during the on and off state of the transistor circuit to enable or disable a waveform that produces the corresponding RF bursts necessary to transmit to the external (or remotely implanted) handheld treatment device 1. The antenna(s) 238 may be connected to electrodes 254 in contact with tissue to provide a return path for the transmitted signal. An A/D (not shown) converter can be used to transfer stored data to a serialized pattern that can be transmitted on the pulse modulated signal from the internal antenna(s) 238 of the neural stimulator.

A telemetry signal from the implanted neural stimulator 10 may include stimulus parameters such as the power or the amplitude of the current that is delivered to the tissue from the electrodes. The feedback signal can be transmitted to the handheld treatment device 1 to indicate the strength of the stimulus at the nerve bundle by means of coupling the signal to the implanted antenna 238, which radiates the telemetry signal to the external (or remotely implanted) handheld treatment device 1. The feedback signal can include either or both an analog and digital telemetry pulse modulated carrier signal. Data such as stimulation pulse parameters and measured characteristics of stimulator performance can be stored in an internal memory device within the implanted neural stimulator 10, and sent on the telemetry signal. The frequency of the carrier signal may be in the range of at 300 MHz to 8 GHz.

In the feedback subsystem 212, the telemetry signal can be down modulated using demodulator 222 and digitized by being processed through an analog to digital (A/D) converter 220. The digital telemetry signal may then be routed to a CPU 230 with embedded code, with the option to reprogram, to translate the signal into a corresponding current measurement in the tissue based on the amplitude of the received signal. The CPU 230 of the controller subsystem 214 can compare the reported stimulus parameters to those held in local memory 228 to verify the neural stimulator(s) 10 delivered the specified stimuli to tissue. For example, if the stimulator reports a lower current than was specified, the power level from the handheld treatment device 1 can be increased so that the implanted neural stimulator 10 will have more available power for stimulation. The implanted neural stimulator 10 can generate telemetry data in real time, for example, at a rate of 8 kbits per second. All feedback data received from the implanted neural stimulator 10 can be logged against time and sampled to be stored for retrieval to a remote monitoring system accessible by the health care professional for trending and statistical correlations.

The sequence of remotely programmable RF signals received by the internal antenna(s) 238 may be conditioned into waveforms that are controlled within the implantable neural stimulator 10 by the control subsystem 242 and routed to the appropriate electrodes 254 that are placed in proximity to the tissue to be stimulated. For instance, the RF signal transmitted from the handheld treatment device 1 may be received by implanted antenna 238 and processed by circuitry, such as waveform conditioning circuitry 240, within the implanted wireless neural stimulator 10 to be converted into electrical pulses applied to the electrodes 254 through electrode interface 252. In some implementations, the implanted neural stimulator 10 contains between two to sixteen electrodes 254.

The waveform conditioning circuitry 240 may include a rectifier 244, which rectifies the signal received by the implanted antenna 238. The rectified signal may be fed to the controller 242 for receiving encoded instructions from handheld treatment device 1. The rectifier signal may also be fed to a charge balance component 246 that is configured to create one or more electrical pulses based such that the one or more electrical pulses result in a substantially zero net charge at the one or more electrodes (that is, the pulses are charge balanced). The charge-balanced pulses are passed through the current limiter 248 to the electrode interface 252, which applies the pulses to the electrodes 254 as appropriate.

The current limiter 248 insures the current level of the pulses applied to the electrodes 254 is not above a threshold current level. In some implementations, an amplitude (for example, current level, voltage level, or power level) of the received RF pulse directly determines the amplitude of the stimulus. In this case, it may be particularly beneficial to include current limiter 248 to prevent excessive current or charge being delivered through the electrodes, although current limiter 248 may be used in other implementations where this is not the case. Generally, for a given electrode having several square millimeters surface area, it is the charge per phase that should be limited for safety (where the charge delivered by a stimulus phase is the integral of the current). But, in some cases, the limit can instead be placed on the current, where the maximum current multiplied by the maximum possible pulse duration is less than or equal to the maximum safe charge. More generally, the limiter 248 acts as a charge limiter that limits a characteristic (for example, current or duration) of the electrical pulses so that the charge per phase remains below a threshold level (typically, a safe-charge limit).

In the event the implanted wireless neural stimulator 10 receives a "strong" pulse of RF power sufficient to generate a stimulus that would exceed the predetermined safe-charge limit, the current limiter 248 can automatically limit or "clip" the stimulus phase to maintain the total charge of the phase within the safety limit. The current limiter 248 may be a passive current limiting component that cuts the signal to the electrodes 254 once the safe current limit (the threshold current level) is reached. Alternatively, or additionally, the current limiter 248 may communicate with the electrode interface 252 to turn off all electrodes 254 to prevent tissue damaging current levels.

A clipping event may trigger a current limiter feedback control mode. The action of clipping may cause the controller to send a threshold power data signal to the handheld treatment device 1. The feedback subsystem 212 detects the threshold power signal and demodulates the signal into data that is communicated to the controller subsystem 214. The controller subsystem 214 algorithms may act on this current-limiting condition by specifically reducing the RF power generated by the RF pulse generator, or cutting the power completely. In this way, the handheld treatment device 1 can reduce the RF power delivered to the body if the implanted neural stimulator 10 reports it is receiving excess RF power.

The controller 250 of the neural stimulator 10 may communicate with the electrode interface 252 to control various aspects of the electrode setup and pulses applied to the electrodes 254. The electrode interface 252 may act as a multiplex and control the polarity and switching of each of the electrodes 254. For instance, in some implementations, the wireless stimulator 10 has multiple electrodes 254 in contact with tissue, and for a given stimulus the handheld treatment device 1 can arbitrarily assign one or more electrodes to 1) act as a stimulating electrode, 2) act as a return electrode, or 3) be inactive by communication of assignment sent wirelessly with the parameter instructions, which the controller 250 uses to set electrode interface 252 as appropriate. It may be physiologically advantageous to assign, for example, one or two electrodes as stimulating electrodes and to assign all remaining electrodes as return electrodes.

In some implementations, for a given stimulus pulse, the controller 250 may control the electrode interface 252 to divide the current arbitrarily (or according to instructions from handheld treatment device 1) among the designated stimulating electrodes. This control over electrode assignment and current control can be advantageous because in practice the electrodes 254 may be spatially distributed along various neural structures, and through strategic selection of the stimulating electrode location and the proportion of current specified for each location, the aggregate current distribution in tissue can be modified to selectively activate specific neural targets. This strategy of current steering can improve the therapeutic effect for the patient.

In another implementation, the time course of stimuli may be arbitrarily manipulated. A given stimulus waveform may be initiated at a time T_start and terminated at a time T_final, and this time course may be synchronized across all stimulating and return electrodes; further, the frequency of repetition of this stimulus cycle may be synchronous for all the electrodes. However, controller 250, on its own or in response to instructions from handheld treatment device 1, can control electrode interface 252 to designate one or more subsets of electrodes to deliver stimulus waveforms with non-synchronous start and stop times, and the frequency of repetition of each stimulus cycle can be arbitrarily and independently specified.

For example, a stimulator having eight electrodes may be configured to have a subset of five electrodes, called set A, and a subset of three electrodes, called set B. Set A might be configured to use two of its electrodes as stimulating electrodes, with the remainder being return electrodes. Set B might be configured to have just one stimulating electrode. The controller 250 could then specify that set A deliver a stimulus phase with 3 mA current for a duration of 200 us followed by a 400 us charge-balancing phase. This stimulus cycle could be specified to repeat at a rate of 60 cycles per second. Then, for set B, the controller 250 could specify a stimulus phase with 1 mA current for duration of 500 us followed by a 800 us charge-balancing phase. The repetition rate for the set-B stimulus cycle can be set independently of set A, say for example it could be specified at 25 cycles per second. Or, if the controller 250 was configured to match the repetition rate for set B to that of set A, for such a case the controller 250 can specify the relative start times of the stimulus cycles to be coincident in time or to be arbitrarily offset from one another by some delay interval.

In some implementations, the controller 250 can arbitrarily shape the stimulus waveform amplitude, and may do so in response to instructions from handheld treatment device 1. The stimulus phase may be delivered by a constant-current source or a constant-voltage source, and this type of control may generate characteristic waveforms that are static, e.g. a constant-current source generates a characteristic rectangular pulse in which the current waveform has a very steep rise, a constant amplitude for the duration of the stimulus, and then a very steep return to baseline. Alternatively, or additionally, the controller 250 can increase or decrease the level of current at any time during the stimulus phase and/or during the charge-balancing phase. Thus, in some implementations, the controller 250 can deliver arbitrarily shaped stimulus waveforms such as a triangular pulse, sinusoidal pulse, or Gaussian pulse for example. Similarly, the charge-balancing phase can be arbitrarily amplitude-shaped, and similarly a leading anodic pulse (prior to the stimulus phase) may also be amplitude-shaped.

As described above, neural stimulator 10 may include a charge-balancing component 246. Generally, for constant current stimulation pulses, pulses should be charge balanced by having the amount of cathodic current should equal the amount of anodic current, which is typically called biphasic stimulation. Charge density is the amount of current times the duration it is applied, and is typically expressed in the units $uC/cm^2$. In order to avoid the irreversible electrochemical reactions such as pH change, electrode dissolution as well as tissue destruction, no net charge should appear at the electrode-electrolyte interface, and it is generally acceptable to have a charge density less than 30 $uC/cm^2$. Biphasic stimulating current pulses ensure that no net charge appears at the electrode after each stimulation cycle and the electrochemical processes are balanced to prevent net dc currents. Neural stimulator 10 may be designed to ensure that the resulting stimulus waveform has a net zero charge. Charge balanced stimuli are thought to have minimal damaging effects on tissue by reducing or eliminating electrochemical reaction products created at the electrode-tissue interface.

A stimulus pulse may have a negative-voltage or current, called the cathodic phase of the waveform. Stimulating electrodes may have both cathodic and anodic phases at different times during the stimulus cycle. An electrode that delivers a negative current with sufficient amplitude to stimulate adjacent neural tissue is called a "stimulating electrode." During the stimulus phase the stimulating electrode acts as a current sink. One or more additional electrodes act as a current source and these electrodes are called "return electrodes." Return electrodes are placed elsewhere in the tissue at some distance from the stimulating electrodes. When a typical negative stimulus phase is delivered to tissue at the stimulating electrode, the return electrode has a positive stimulus phase. During the subsequent charge-balancing phase, the polarities of each electrode are reversed.

In some implementations, the charge balance component 246 uses a blocking capacitor(s) placed electrically in series with the stimulating electrodes and body tissue, between the point of stimulus generation within the stimulator circuitry and the point of stimulus delivery to tissue. In this manner, a resistor-capacitor (RC) network may be formed. In a multi-electrode stimulator, one charge-balance capacitor(s) may be used for each electrode or a centralized capacitor(s) may be used within the stimulator circuitry prior to the point of electrode selection. The RC network can block direct current (DC), however it can also prevent low-frequency alternating current (AC) from passing to the tissue. The frequency below which the series RC network essentially blocks signals is commonly referred to as the cutoff frequency, and in one embodiment the design of the stimulator system may ensure the cutoff frequency is not above the fundamental frequency of the stimulus waveform. In this embodiment, the wireless stimulator may have a charge-balance capacitor with a value chosen according to the measured series resistance of the electrodes and the tissue environment in which the stimulator is implanted. By selecting a specific capacitance value the cutoff frequency of the RC network in this embodiment is at or below the fundamental frequency of the stimulus pulse.

In other implementations, the cutoff frequency may be chosen to be at or above the fundamental frequency of the stimulus, and in this scenario the stimulus waveform created prior to the charge-balance capacitor, called the drive waveform, may be designed to be non-stationary, where the envelope of the drive waveform is varied during the duration of the drive pulse. For example, in one embodiment, the initial amplitude of the drive waveform is set at an initial amplitude Vi, and the amplitude is increased during the duration of the pulse until it reaches a final value k*Vi. By changing the amplitude of the drive waveform over time, the shape of the stimulus waveform passed through the charge-balance capacitor is also modified. The shape of the stimulus waveform may be modified in this fashion to create a physiologically advantageous stimulus.

In some implementations, the wireless neural stimulator 10 may create a drive-waveform envelope that follows the envelope of the RF pulse received by the receiving dipole antenna(s) 238. In this case, the handheld treatment device 1 can directly control the envelope of the drive waveform within the wireless neural stimulator 10, and thus no energy storage may be required inside the stimulator itself. In this implementation, the stimulator circuitry may modify the envelope of the drive waveform or may pass it directly to the charge-balance capacitor and/or electrode-selection stage.

In some implementations, the implanted neural stimulator 10 may deliver a single-phase drive waveform to the charge balance capacitor or it may deliver multiphase drive waveforms. In the case of a single-phase drive waveform, for example, a negative-going rectangular pulse, this pulse comprises the physiological stimulus phase, and the charge-balance capacitor is polarized (charged) during this phase. After the drive pulse is completed, the charge balancing function is performed solely by the passive discharge of the charge-balance capacitor, where is dissipates its charge through the tissue in an opposite polarity relative to the preceding stimulus. In one implementation, a resistor within the stimulator facilitates the discharge of the charge-balance capacitor. In some implementations, using a passive discharge phase, the capacitor may allow virtually complete discharge prior to the onset of the subsequent stimulus pulse.

In the case of multiphase drive waveforms the wireless stimulator may perform internal switching to pass negative-going or positive-going pulses (phases) to the charge-balance capacitor. These pulses may be delivered in any sequence and with varying amplitudes and waveform shapes to achieve a desired physiological effect. For example, the stimulus phase may be followed by an actively driven charge-balancing phase, and/or the stimulus phase may be preceded by an opposite phase. Preceding the stimulus with an opposite-polarity phase, for example, can have the advantage of reducing the amplitude of the stimulus phase required to excite tissue.

In some implementations, the amplitude and timing of stimulus and charge-balancing phases is controlled by the amplitude and timing of RF pulses from the handheld treatment device 1, and in others this control may be administered internally by circuitry onboard the wireless stimulator 10, such as controller 250.

Referring to FIGS. 3A-3G, an example of handheld treatment device 1 includes a handheld housing that has a top portion 304 and a bottom portion 300. The bottom portion 300 is generally rectangular in shape, and includes a top surface 310, a bottom surface 320, and a first side surface 307A, a second side surface 307B, a third side surface 307C, and a fourth side surface 307D that connect the top surface 310 to the bottom surface 320. The first side surface 307A, the second side surface 307B, the third side surface 307C, and the fourth side surface 307D are connected to one another by rounded corners 305A, 305B, 305C, and 305D. Screws 309A to 309D are placed in holes generally located near corners 305A to 305D to tie various parts of the bottom portion 300, as discussed below (for example, in association with FIGS. 4B to 4E).

The top portion 303 includes a handle member 308. The handle member 308 includes a vertical portion 302 and a horizontal portion 304. The vertical portion 302 includes a first end 322A and a second end 322B. The first end 322A is coupled to the top surface 310, and the vertical portion 302 extends from the first end 322A to the second end 322B along a longitudinal axis 322C that is perpendicular to the top surface 310. Control panel 306 is located between the first and second ends 322A and 322B. The horizontal portion 304 includes a first end 328A coupled to the second end 322B of the vertical portion 302. The horizontal portion 304 also includes a second end 328B. The horizontal portion 304 extends from the first end 328A to the second end 328B along a longitudinal axis 328C that is parallel to the top surface 310. The horizontal portion 304 has a length such that the second end 328B of the horizontal portion 308 extends slightly beyond the side surface 307A. Other configurations not shown allow the length of horizontal portion 304 to be chosen differently.

Accordingly, the vertical portion 302 and the horizontal portion 304 form an L-shaped handle member 308 that can be held in the hand of a user of the handheld treatment device 1. A control panel 306 is located on a front side 325A of the vertical portion 210 (that is, on the side that is parallel to side surface 307C of the bottom portion 300). The control panel 306 includes interface buttons 326A to 326C that are used to turn the treatment device 1 on and off, as well as to adjust the parameters of the stimulation waveform, such as intensity. The back side 325B of the vertical portion 302 (that is, the side opposite the front side 325A) is curved so as to accommodate the user's fingers.

Figure 3B:
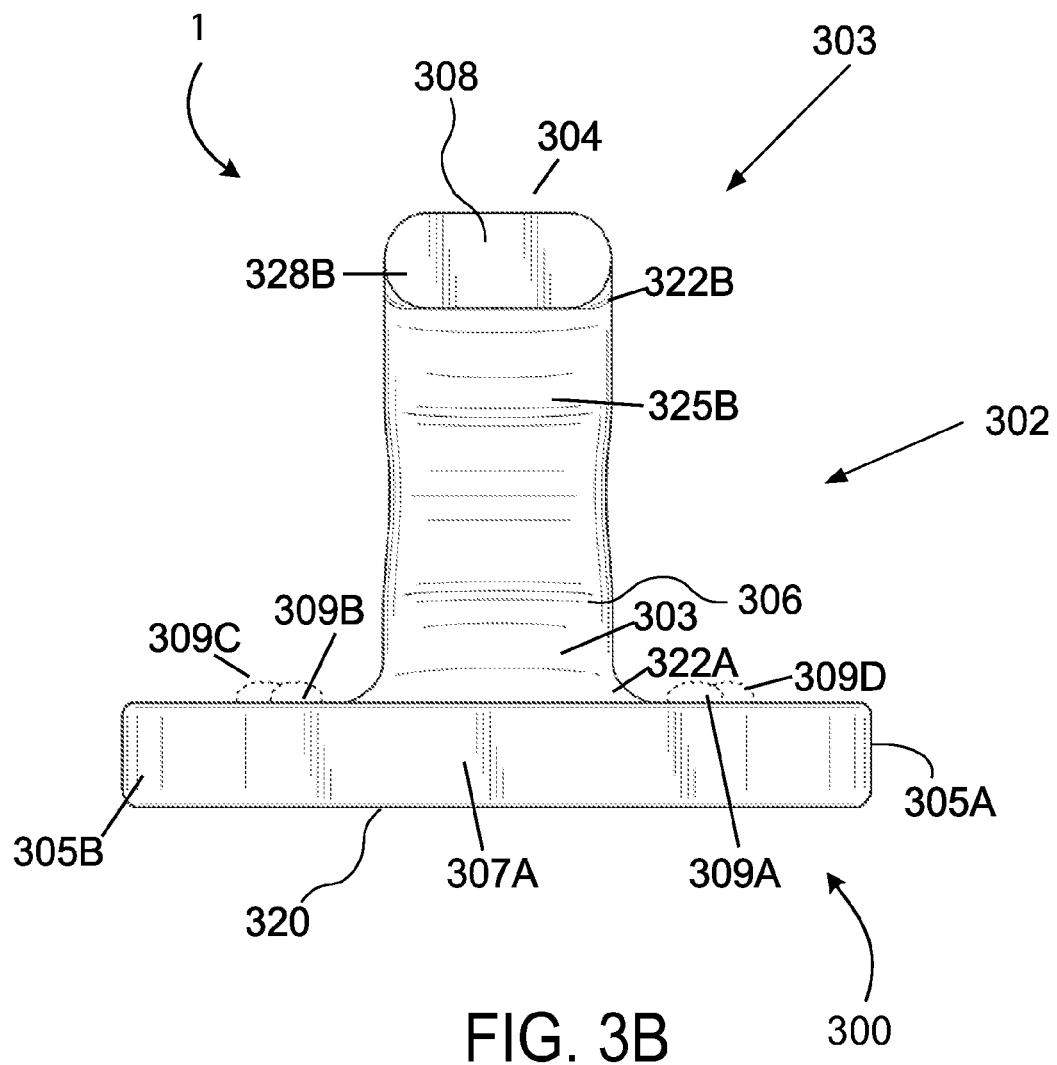
Figure 3C:
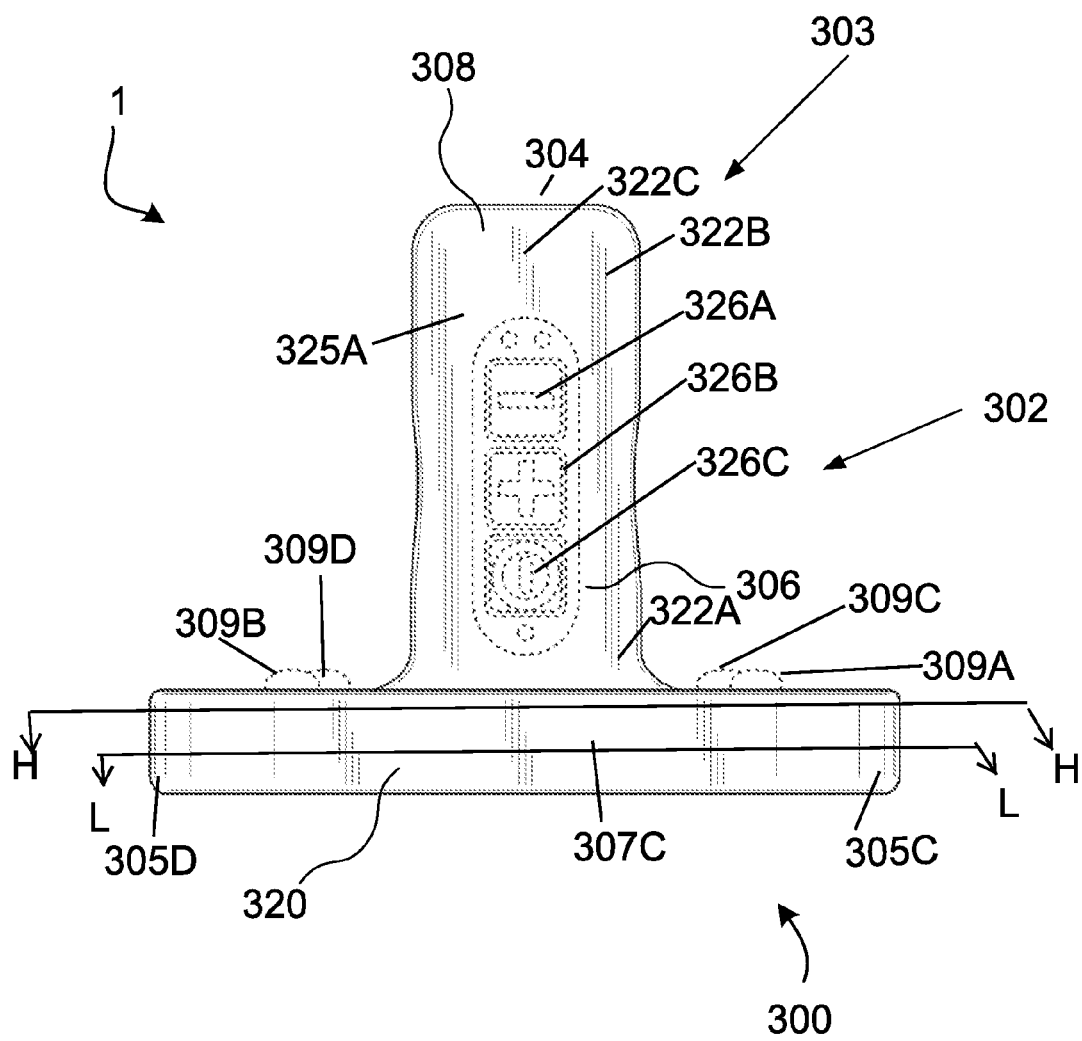
Figure 3D:
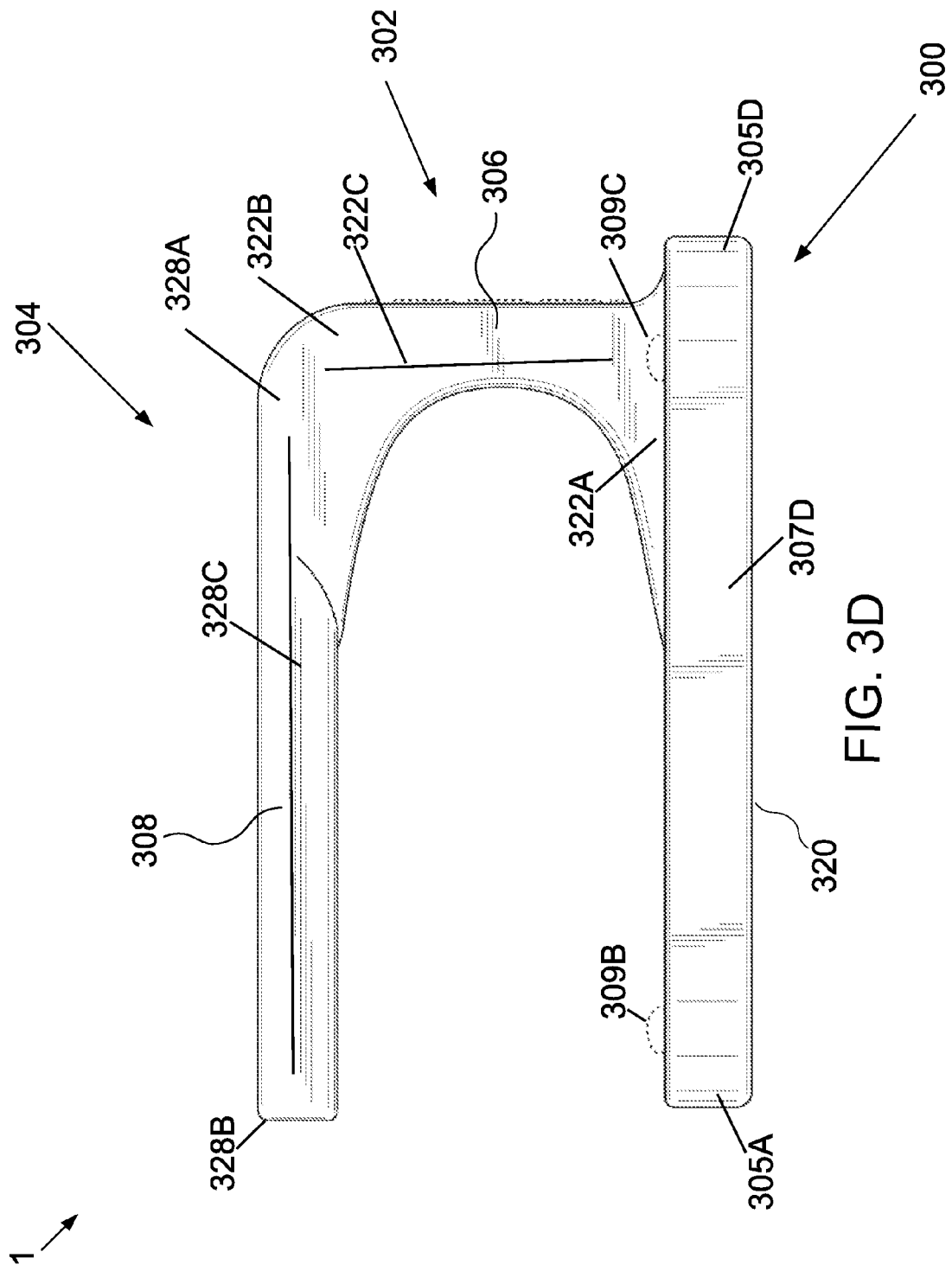
Figure 3F:
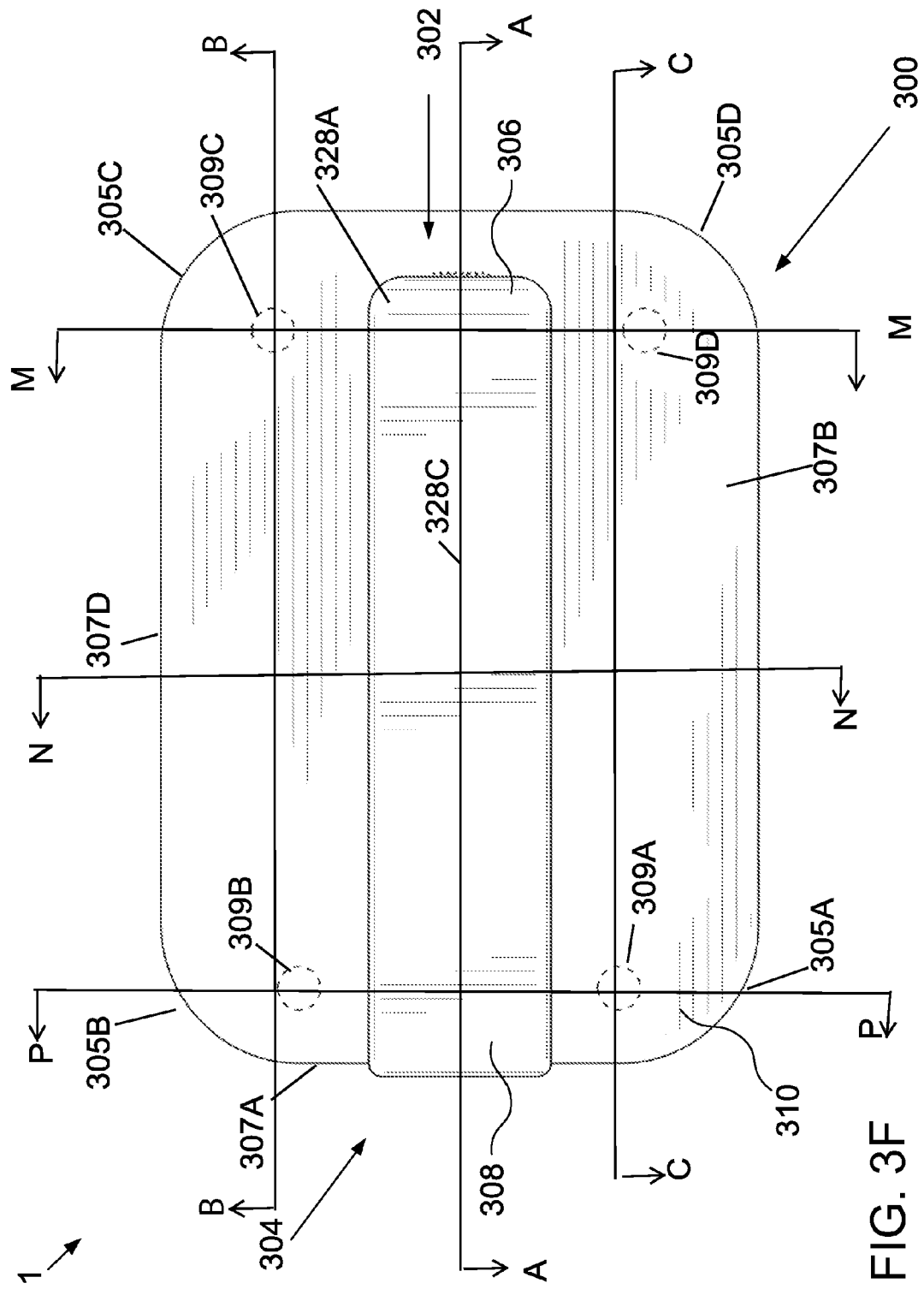
Figure 3G:
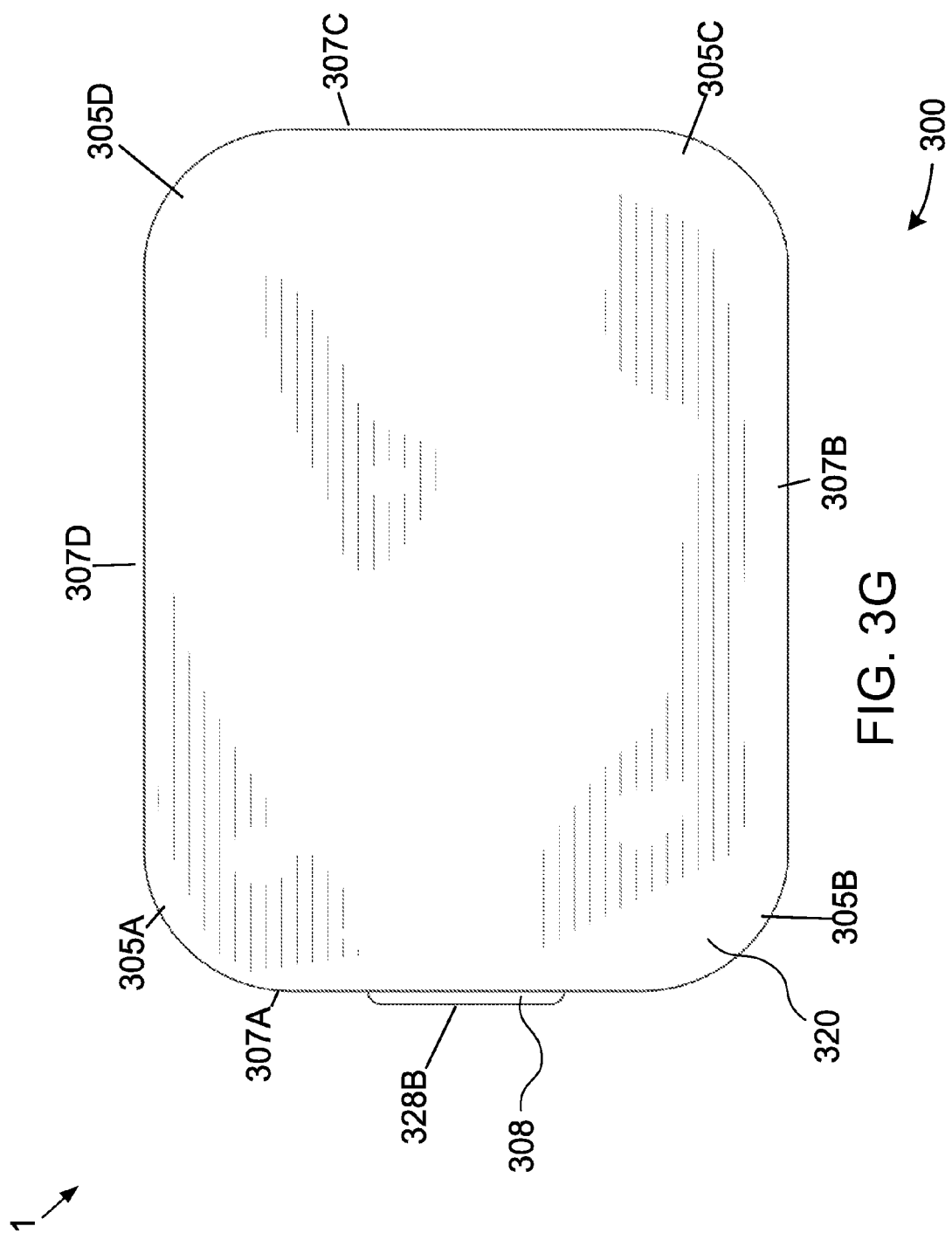
Figure 7A:
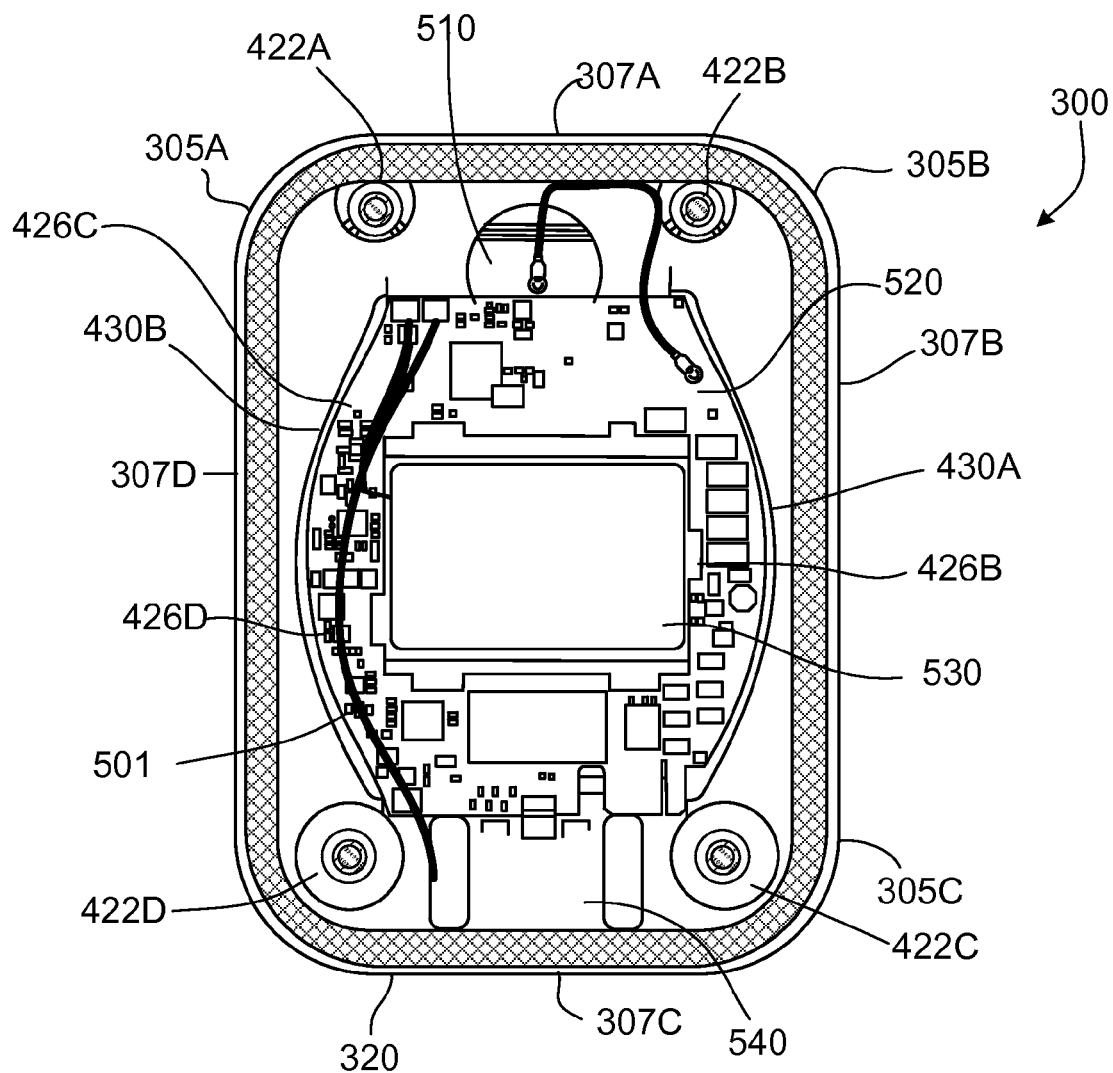
FIGS. 7A to 7B depict top side cutaway views of the handheld treatment device of FIG. 1.
Figure 7B:
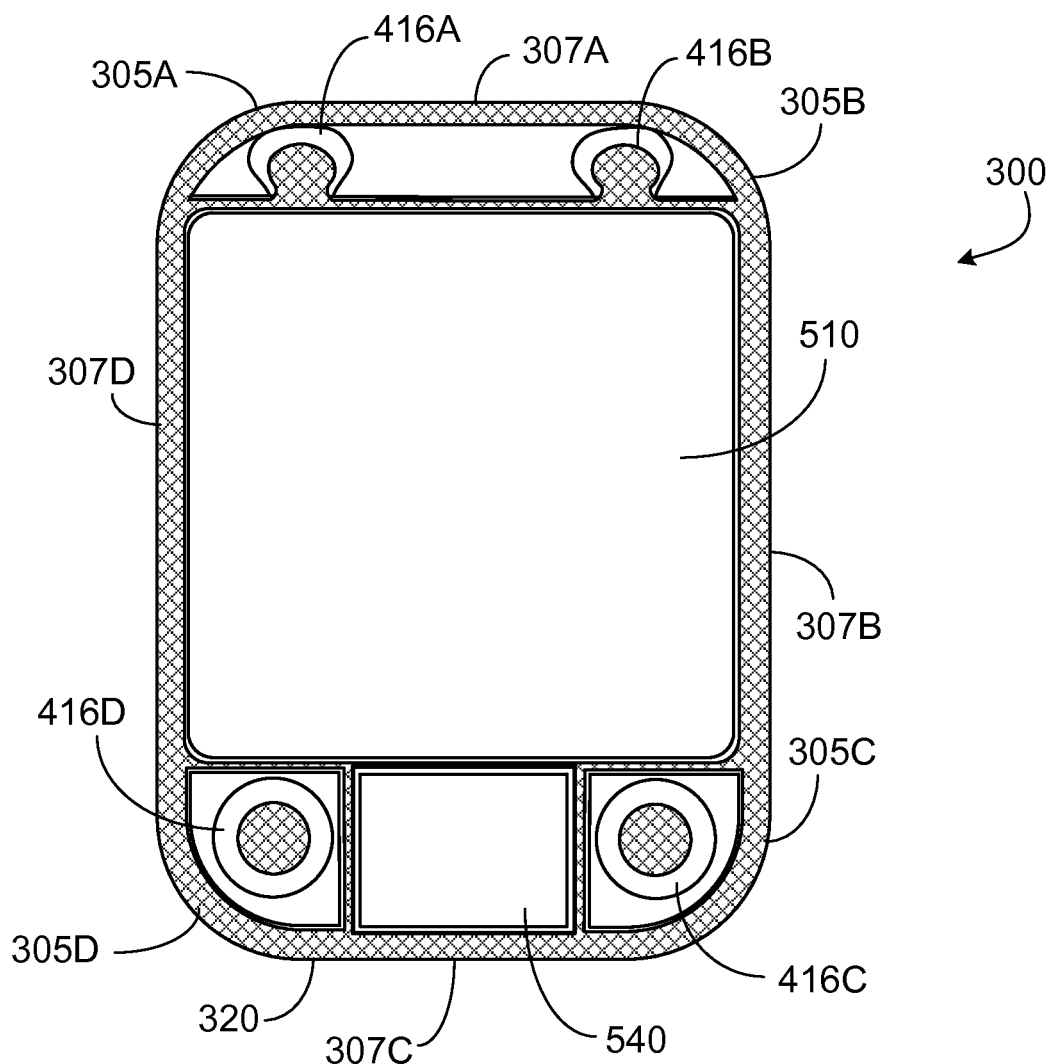
Figure 8A:
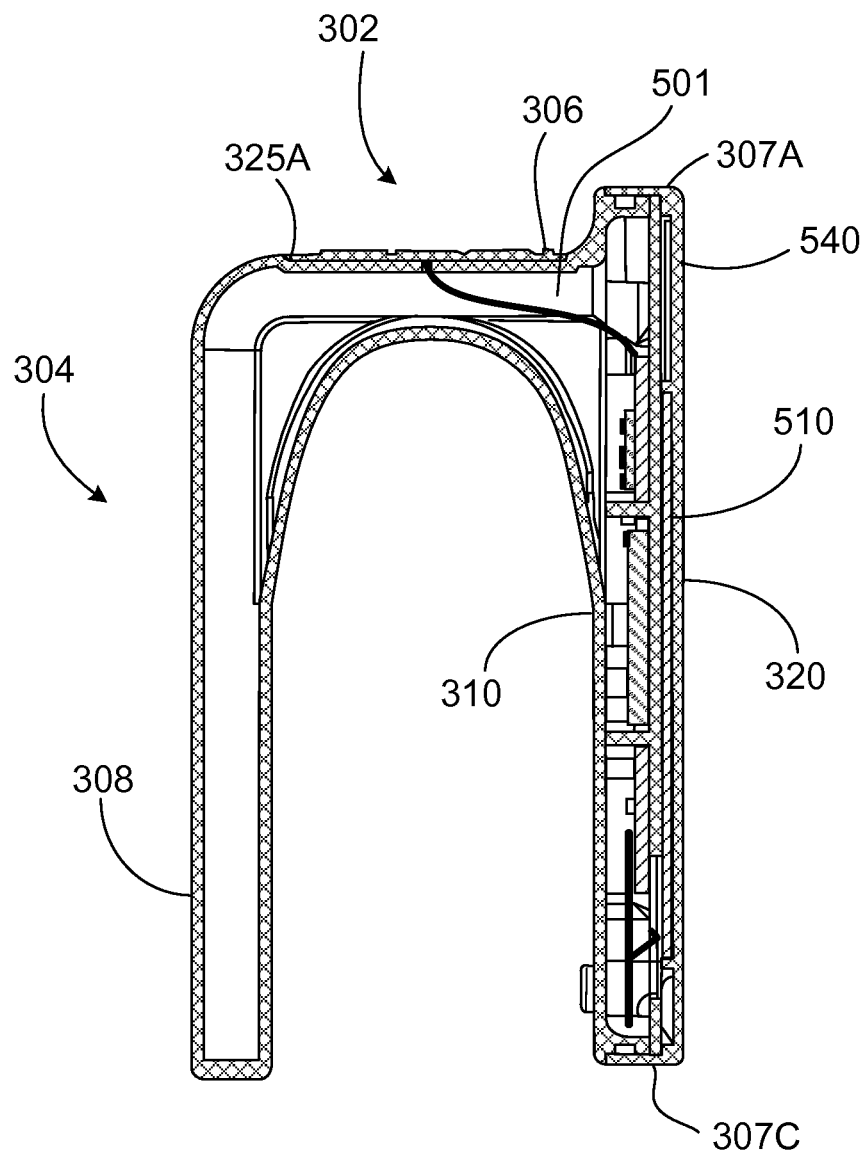
Figure 8E:
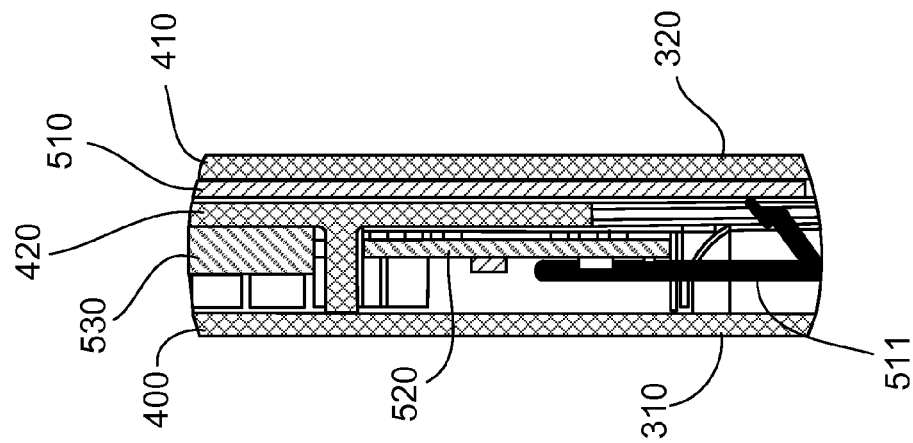
Figure 8D:
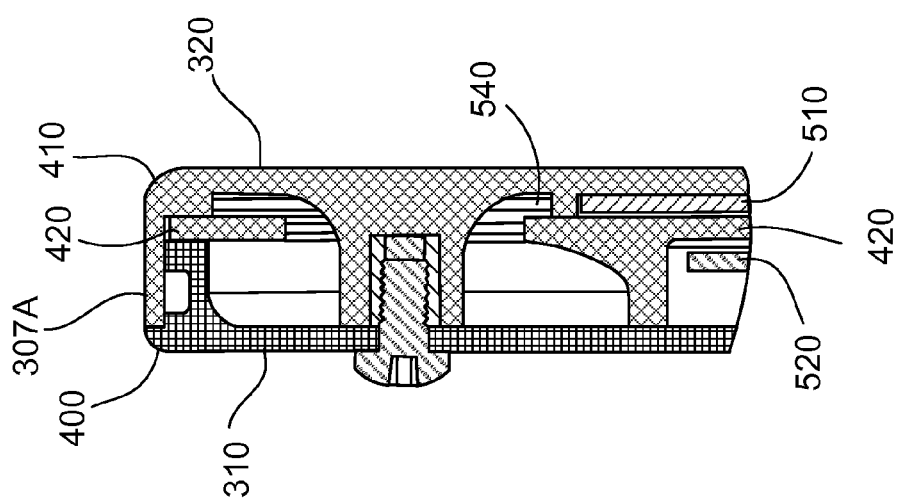
Figure 8F:
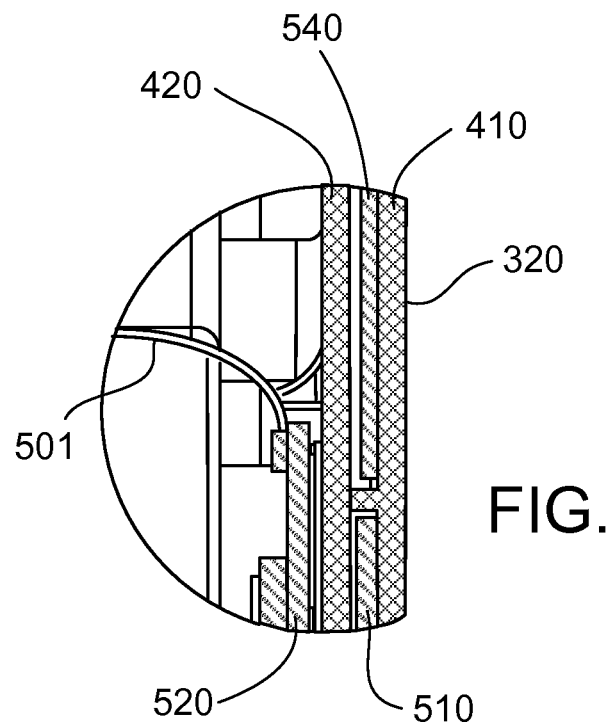
Figure 8G:
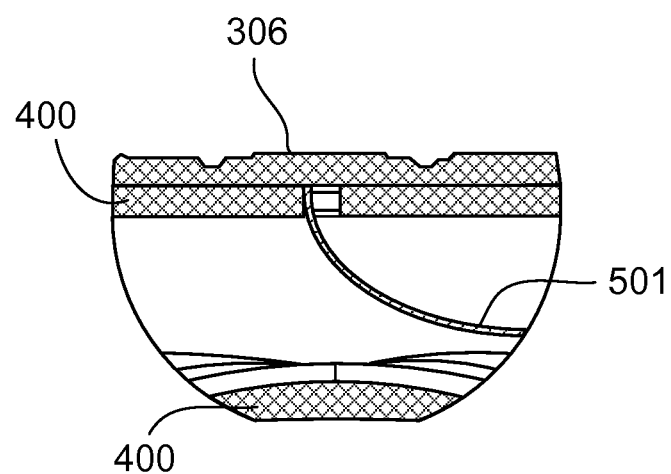
Figure 9A:
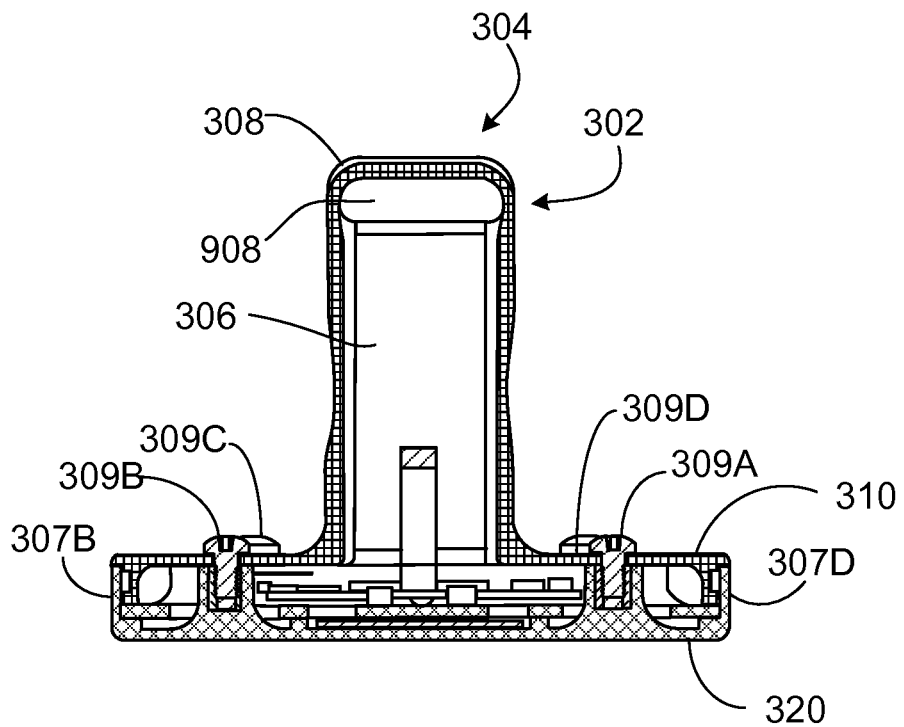
FIGS. 9A to 9F depict various lateral cutaway views of the handheld treatment device of FIG. 1.
Figure 9B:
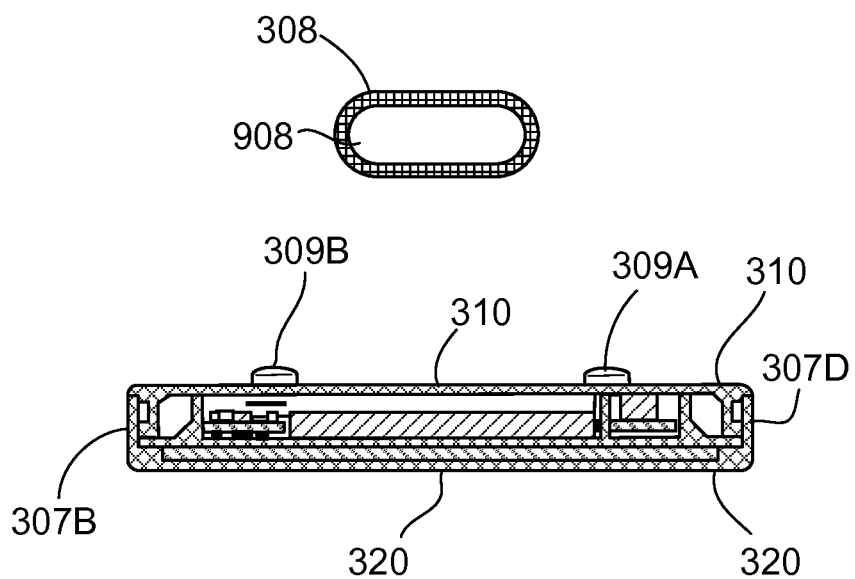
Figure 9C:
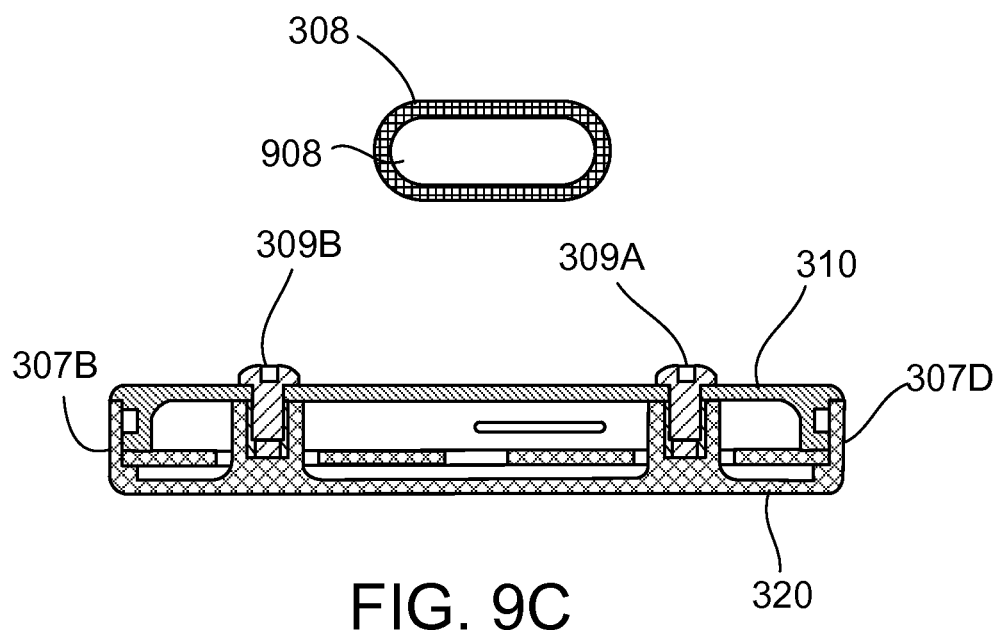

Moreover, FIG. 3C illustrates locations H and L corresponding to two cutaway views as shown in FIGS. 7A and 7B, respectively. FIG. 3F illustrates locations A to C corresponding to three cutaway views parallel to side surfaces of 307B and 307D. These three cutaway views are shown in FIGS. 8A to 8C, respectively. FIG. 3F also illustrates locations M to P corresponding to three cutaway views parallel to side surfaces of 307A and 307C. These three cutaway views are shown in FIGS. 9A to 9C, respectively.

Figure 4A:
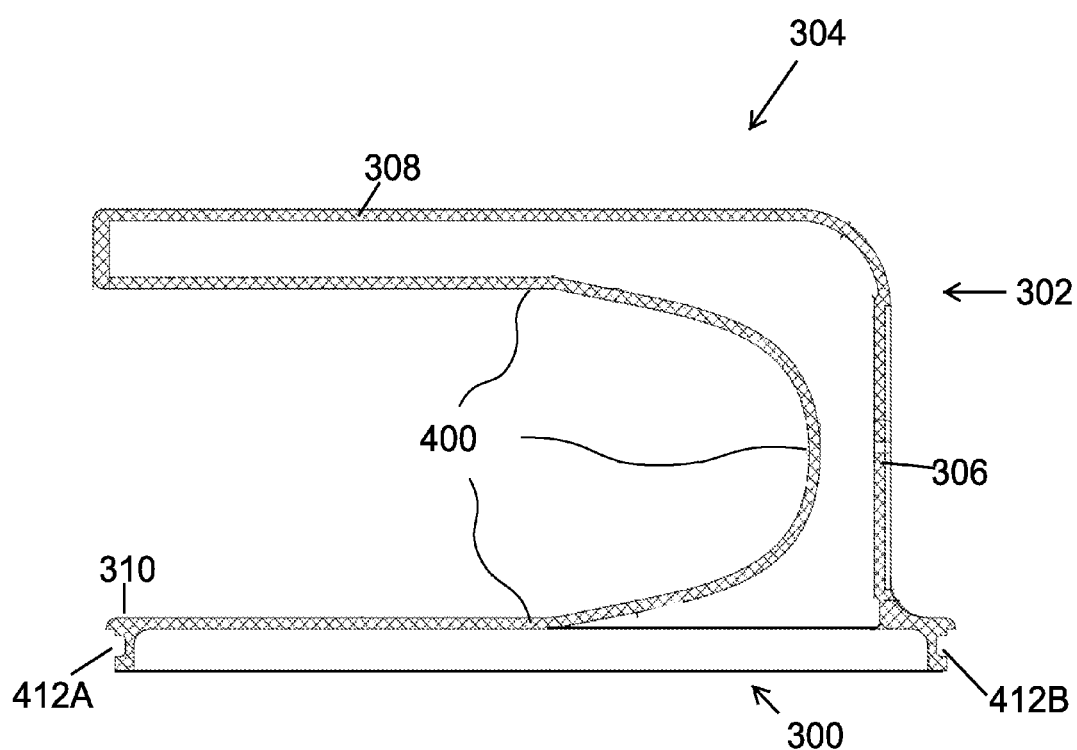

Referring to FIGS. 4A-4C, the housing for handheld treatment device 1 includes a cover segment 400, a middle segment 420, and a bottom segment 410. Some implementations may not include a middle segment. The cover segment 400 is generally hollow and defines the handle member 303 that includes a vertical portion 302 and a horizontal portion 308. As illustrated in FIG. 4A, cover segment 400 includes top surface 310 and sidewall 412. Side wall 412 mates with portions of the middle segment 420 and the bottom segment 410 to form the bottom portion 300 of device 1. The cover segment 400 further includes screw holes (not shown in FIG. 4A) to accommodate screws 309A to 309D.

Figure 4D:
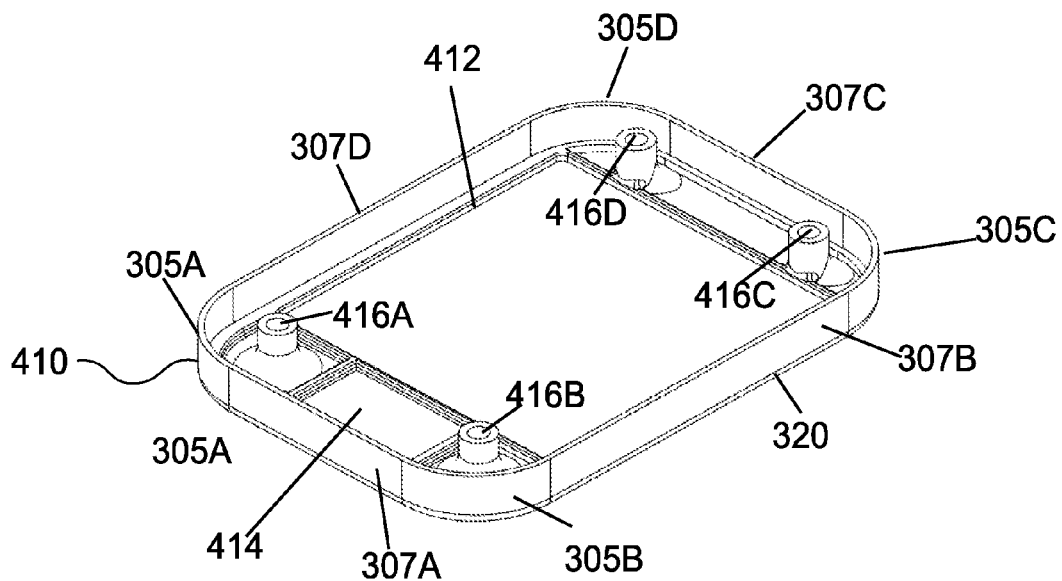

FIGS. 4B and 4D respectively illustrate a cutaway view and a perspective view of bottom segment 410. Bottom segment 410 forms part of bottom portion 300 including bottom surface 320, sidewalls 307A to 307D, and round corners 305A to 305D. Within the confines of sidewalls 307A to 307D, bottom segment 410 includes walls that define a charging coil recess 414 and an antenna recess 412, and includes four screw receptacles 416A to 416D, each of which is positioned near one of the corners 305A to 305D. Charging coil recess 414 is where the charging coil (shown as 540 in, for example, FIG. 5A) is seated. Antenna recess 412 is the place where the antenna (shown as 510 in, for example, FIG. 5A), for example, a patch antenna, is seated. Screw receptacles 416A to 416D are hollow cylinders that are tapped and threaded holes for holding screws that mechanically tie the bottom segment 410 to top segment 400 and middle segment 420.

Figure 4E:
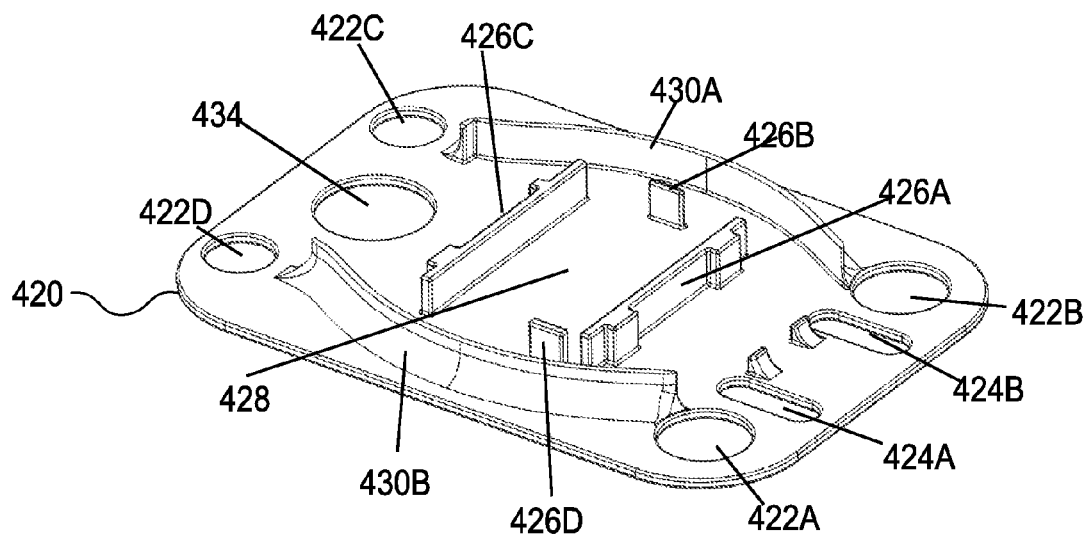

FIGS. 4C and 4E respectively illustrate a cutaway view and a perspective view of middle segment 420. Middle segment 420 sits between top segment 400 and bottom segment 410, and covers the antenna and charging coil placed in the charging coil recess 414 and antenna recess 412, respectively, as described below. Middle segment 420 includes screw receptacle holes 422A to 422D that are aligned with screw receptacles 416A to 416D on the bottom segment 420 and the screw holes on the top segment for the retaining screws to reach bottom segment 420 from top segment 400. Middle segment 420 further includes battery retaining walls 426A to 426D that define a central battery space 428, in which a battery (shown as 530 in, for example, FIG. 5A) is seated, as described below, when the handheld device 1 is assembled. The battery can be a rechargeable battery. Besides the central battery space 428, circuit board retaining walls 430A and 430B are curved and define a central circuit board and battery space 432, which further retains the circuit board (shown as 520 in, for example, FIG. 5A) for handheld treatment device 1. In alignment with antenna recess 412, middle segment 410 also provides antenna cable access hole 434 for a cable to reach the antenna when the antenna is placed in the antenna recess 412 on bottom segment 420. Similarly, middle segment 410 provides charging cable access hole 424A and 424B for a charging cable to reach the charging coil when the charging cable is placed in the charging coil recess 414 on bottom segment 420.

Figure 5A:
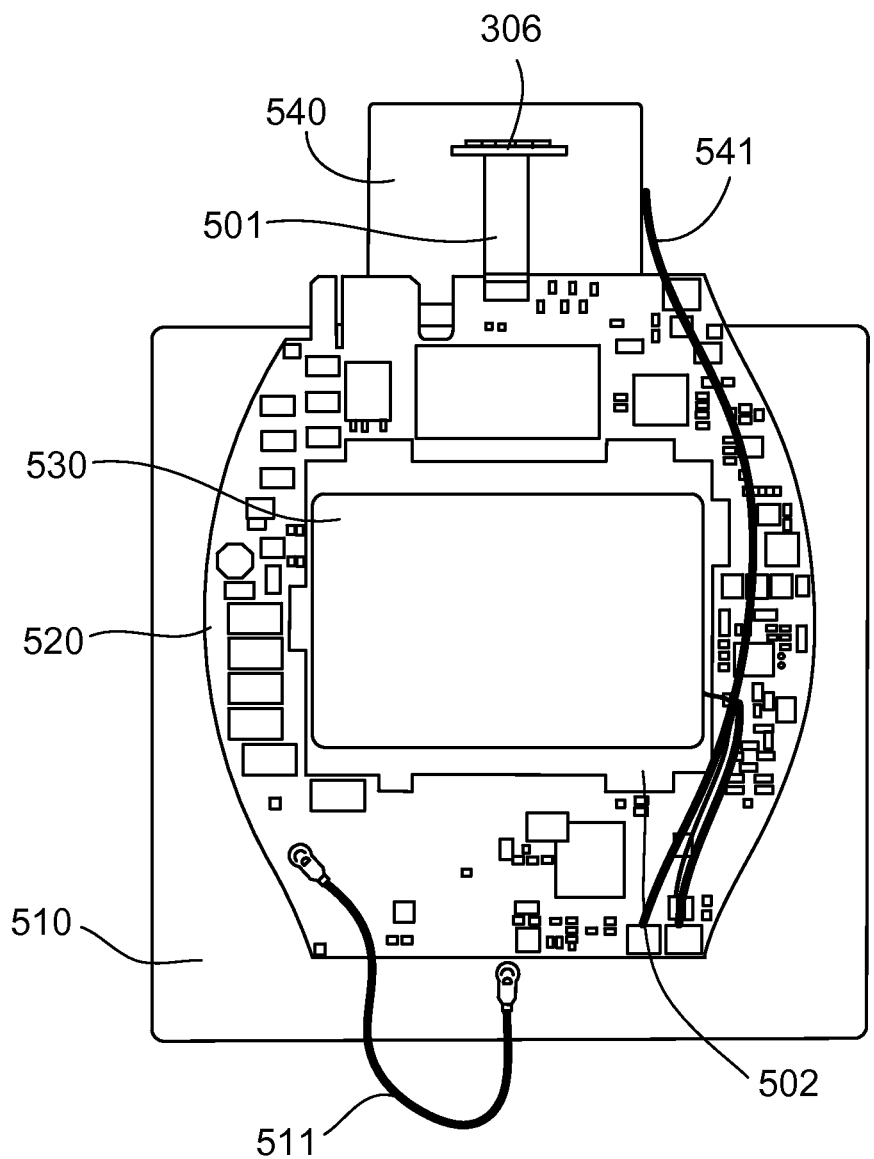
FIGS. 5A to 5C depict the components within the handheld treatment device of FIG. 1.
Figures 5B, 5C:
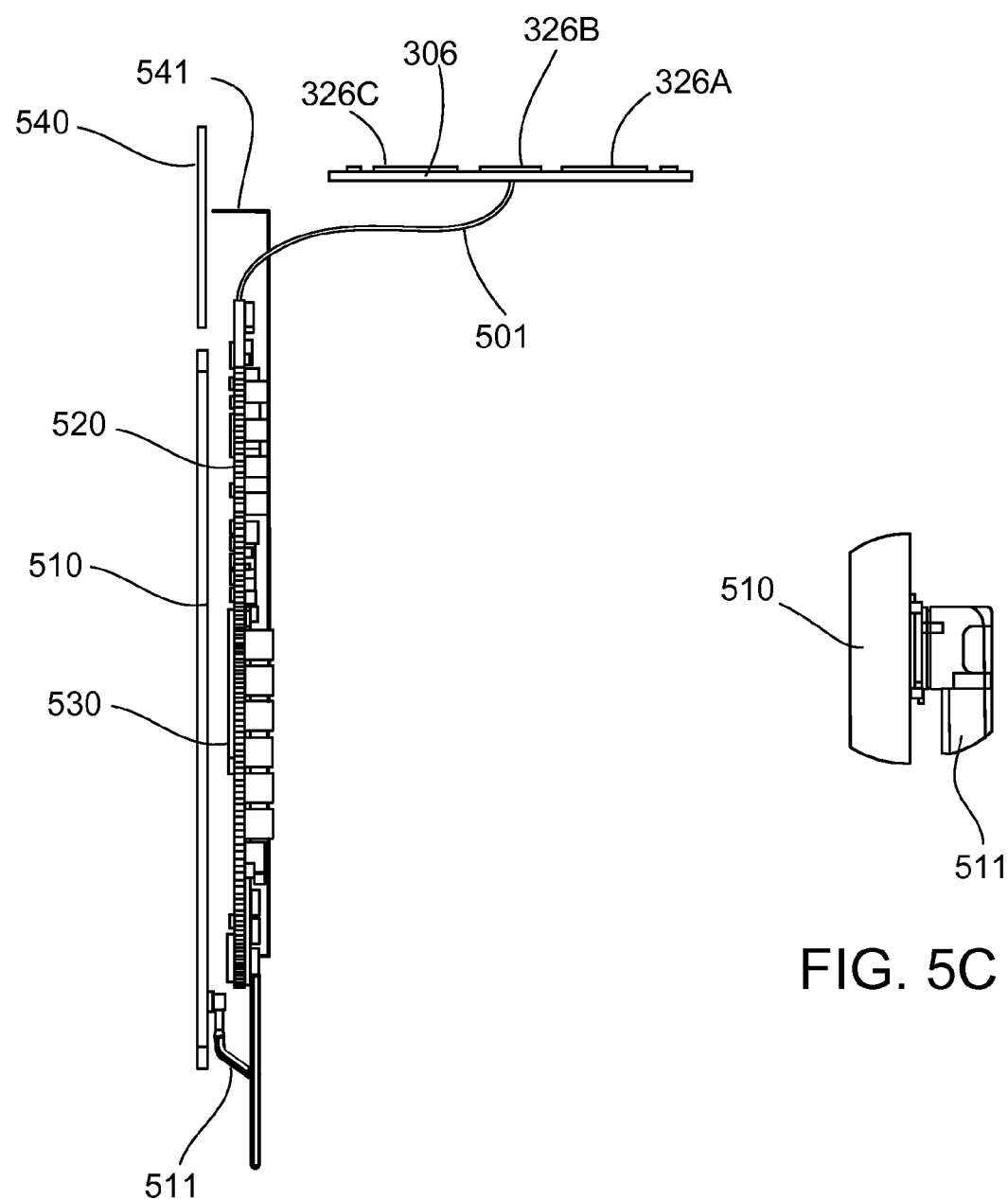

Referring to FIGS. 5A to 5C, the housing for handheld treatment device 1 encloses the antenna 510, a circuit board 520, battery 530, a charging coil 540, and a control panel 306. Antenna 510 is arranged at the bottom of the stack shown. Antenna 510 as shown is a patch antenna, but may be a dipole antenna, spiral antenna, or other antenna configuration with a form factor that fits the bottom portion of handheld treatment device. Antenna 510 is connected to the circuit board 520 via cable 511. The circuit board 520 includes the circuitry that controls the handheld device 1, such as the circuitry shown as part of handheld device 1 in FIG. 2. As described above, this circuitry generates the signals that are transmitted to the neural stimulator 10 through antenna 510. As illustrated, charging coil is connected to circuit board 520 (and accompanying circuitry) via cable 541. The charging coil 540 is a recharging coil that receives energy wirelessly, for example, via inductive coupling and provides that energy, through cable 541, to circuitry that uses the energy to recharge battery 530. In other instances, recharging of battery 530 is accomplished by using a wire, for example, a power cord, or a universal serial bus (USB) cable.

Control panel 306 includes interface buttons 326A to 326C for a user to apply control, including powering on or off handheld treatment device 1, and adjusting parameters of the stimulation waveform, such as intensity. Control panel 306 is connected to circuit board 520 via cable 501.

Circuit board 520 and battery 530 are located on a plane parallel to antenna 510. This plane generally correspond to middle segment 420. As illustrated in FIG. 5A, a central open area 502 is defined in the circuit board 520 so as to accommodate the battery retaining walls 426A to 426D, as well as the battery 530 when the handheld device 1 is assembled.

Figure 6A:
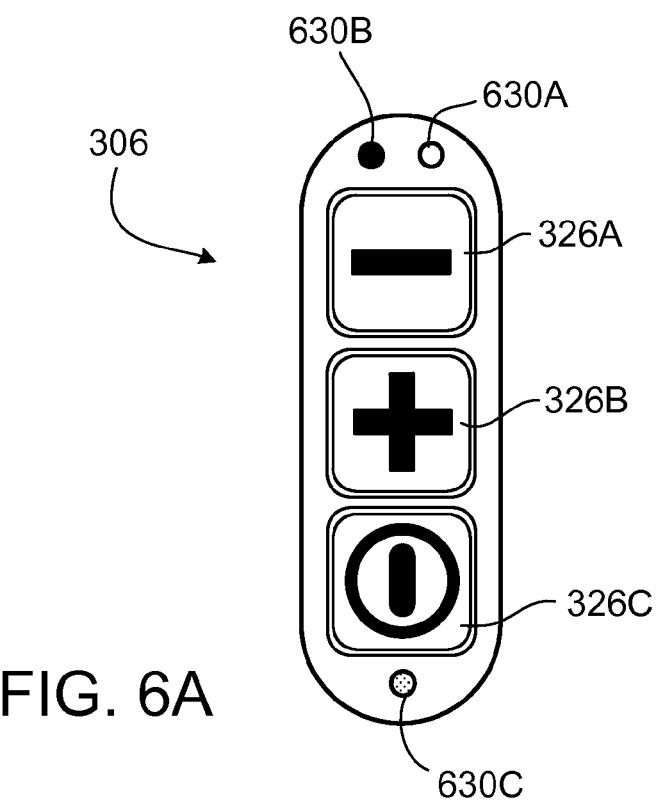
FIGS. 6A to 6B depict an example of a control panel of the handheld treatment device of FIG. 1.

Referring to FIG. 6A, control panel 306 is shown in more detail. Control panel 306 includes interface buttons 326A to 326C and indicators 632A to 632. In some implementations, interface button 326C is used to change the handheld treatment device 1 between an on state and an off state. In some implementations, interface button 326B is used to increase a treatment value, such as amplitude or intensity of stimulation waveform. In some implementations, interface button 326A is used to decrease the treatment value. In some implementations, indicator 630C indicates whether the handheld treatment device 1 is in an on state or an off state. In some implementations, indicator 630B indicates the activation of second interface button 326B. In some implementations, third indicator 630A indicates the activation of interface button 326A.

Figure 6B:
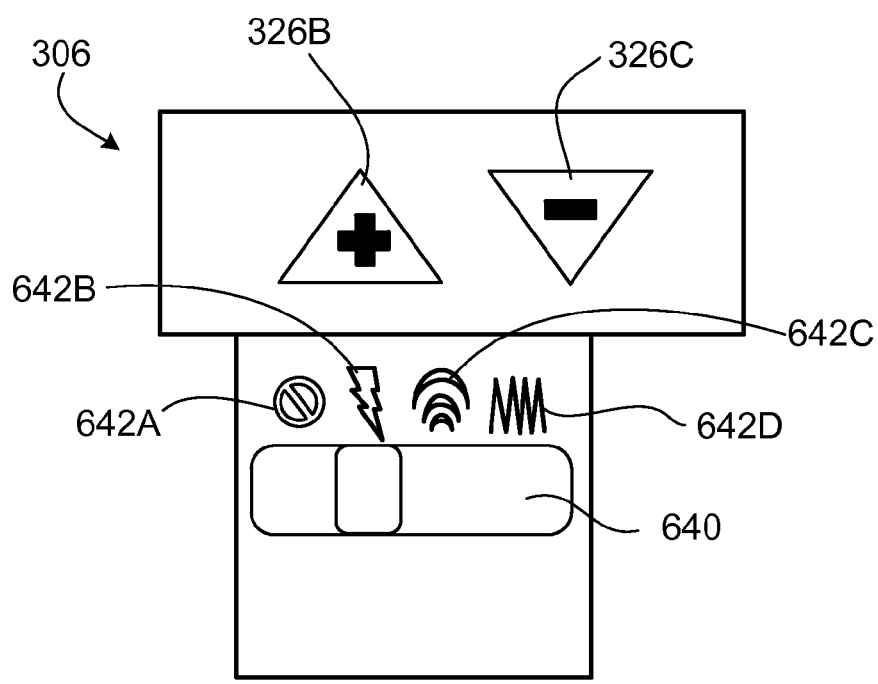

FIG. 6B illustrates another example of interface buttons 326B and 326C. In this example, control panel 306 is a touch screen device and activating either interface button 326B or 326C causes interface button 640 to pop up. Interface button 640 can be used to select a neural stimulation setting from settings 642A to 642D and then adjust by adjusted the setting parameter by interface buttons 326B and 326C. In some implementations, settings 642A to 642D include an amplitude setting, a pulse width setting, a frequency setting, or a preset programs setting.

FIGS. 7A to 7B respectively show the cutaway views at levels H and L as indicated in FIG. 3C. Bottom portion 300 is generally square with rounded corners. Sidewalls 307A to 307D form the four sides of bottom portion 300 while rounded corners 305A to 305D correspond to the four corners of bottom portion 300. Screw receptacle holes 422A to 422D allow the screws to pass through middle segment 420 into screw receptacles 416A to 416D so that segments of the handheld treatment device to be tightened to each other. Battery retaining walls 426A to 426D define the central battery space 428 in which battery 530 is seated. Circuit board 520 is seated in the central circuit board and battery space 432 defined by circuit board retaining walls 430A and 430B, with the central opening 502 of the circuit board accommodating the battery retaining walls 426A to 426D. Charging coil 540 and antenna 510 are located in the charging coil recess 414 and antenna recess 41, respectively, and accordingly located on a plane underneath the plane for circuit board 520 and battery 530. Cable 501 passes through charging cable access hole 424A and connects charging coil 540 to circuit board 520 while cable 511 passes through antenna cable access hole 434 and connects antenna 510 to circuit board 520.

FIGS. 8A to 8C respectively show the cutaway views at levels A to C as indicated in FIG. 3F. Handle member 308 includes horizontal portion 304 and vertical portion 302. Control panel 306 is mounted on front side 325A. Control panel 306 is connected to circuit board 520 through cable 501, which passes through a hollow portion of vertical portion 302. Bottom portion 300 is enclosed by top surface 310, bottom surface 320, side walls 307A and 307C. Bottom portion encloses antenna 510, charging coil 540, battery 530, and circuit board 520. Battery 530 is mounted in a space defined by battery retaining walls 426A to 426D. Battery 530 generally provides power to handheld treatment device 1. Battery 530 is rechargeable, for example, via recharging coil 540. Antenna 510 and charging coil 540 are located on a plane underneath battery 530 and above bottom surface 320. Antenna 510 is placed in antenna recess while charging coil is placed in charging coil recess.

FIGS. 8D to 8G show the zoomed views corresponding to detail circles D, E, F, and G, as indicated on FIGS. 8A and 8B. These zoomed views highlight top segment 400, bottom segment 410, and middle segment 420. Bottom segment 410 may also be known as base housing section, which includes an outer shell with a hollow interior, thereby allowing placement of various functional elements inside handheld treatment device 1 (as discussed above, for example in association with FIGS. 4B and 4D). Middle segment 420 may also be known as antenna cover housing section. Middle segment 410 is placed within the cavity created by the attachment of bottom segment 400 to top segment 400 (as discussed above, for example, in association with FIGS. 4C and 4E). Middle segment 410 may allow the placement of an antenna nearly adjacent to electrical circuitry within handheld treatment device 1 without causing an electrical short or other electrical interference between those components (that is, the middle segment electrically isolates the antenna 510 from the circuit board 520 and battery 530). Top segment 420 may also be known as cover housing section.

These zoomed views also indicate portions of antenna 510, control circuitry 520, battery 530, and charging coil 540. A screw is further shown attaching cover housing section 800 to base housing section 810 through screw hole. Other fastening mechanisms, such as a latching mechanism, may be also used. Cable 501 connects control panel 306 to control circuits 520A and 520B such that signals are communicated from control panel 306 to control circuits 520A and 520B and vice versa.

Figure 9D:
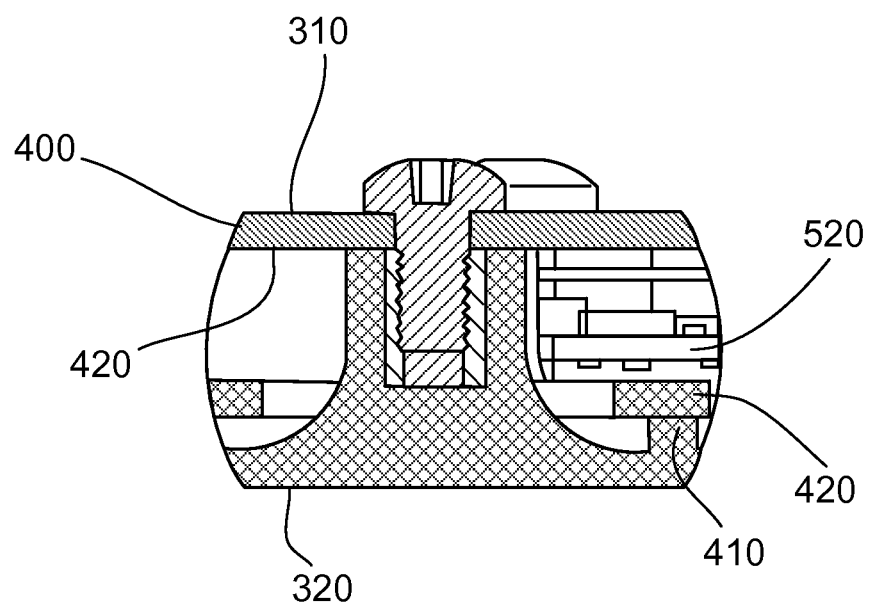
Figure 9E:
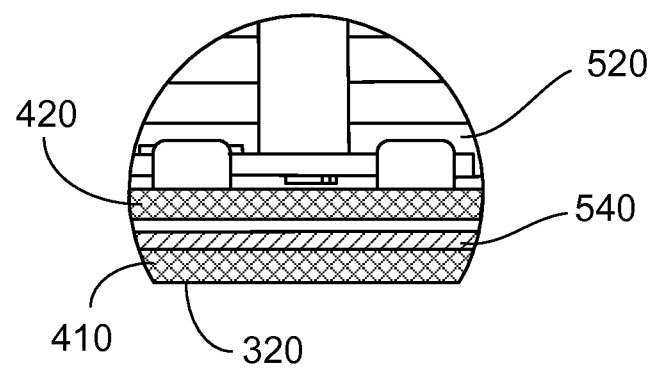
Figure 9F:
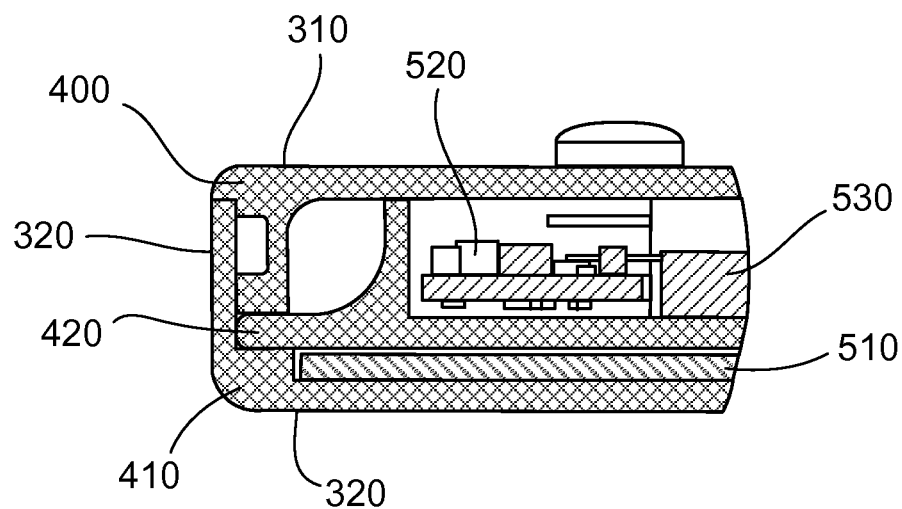

FIGS. 9A to 9C respectively show the cutaway views at levels M to P as indicated in FIG. 3F. FIGS. 9D to 9F show the zoomed views corresponding to detail circles T, U, and V, as indicated on FIG. 9A. Bottom portion 300 is surrounded by top surface 310, bottom surface 320, and side walls 307B and 307D. Screws 309A to 309D fasten the enclosure of the bottom portion 300. Bottom portion 300 encloses circuits 520A to 520B, charging coil 540, antenna 510. The enclosure is buttressed by cover housing section 800, base housing section 810, and antenna cover housing section 820. Handle member 308 includes horizontal portion 304 and vertical portion 302. Horizontal portion 304 includes hollow portion 908 as the interior.

Figure 10A:
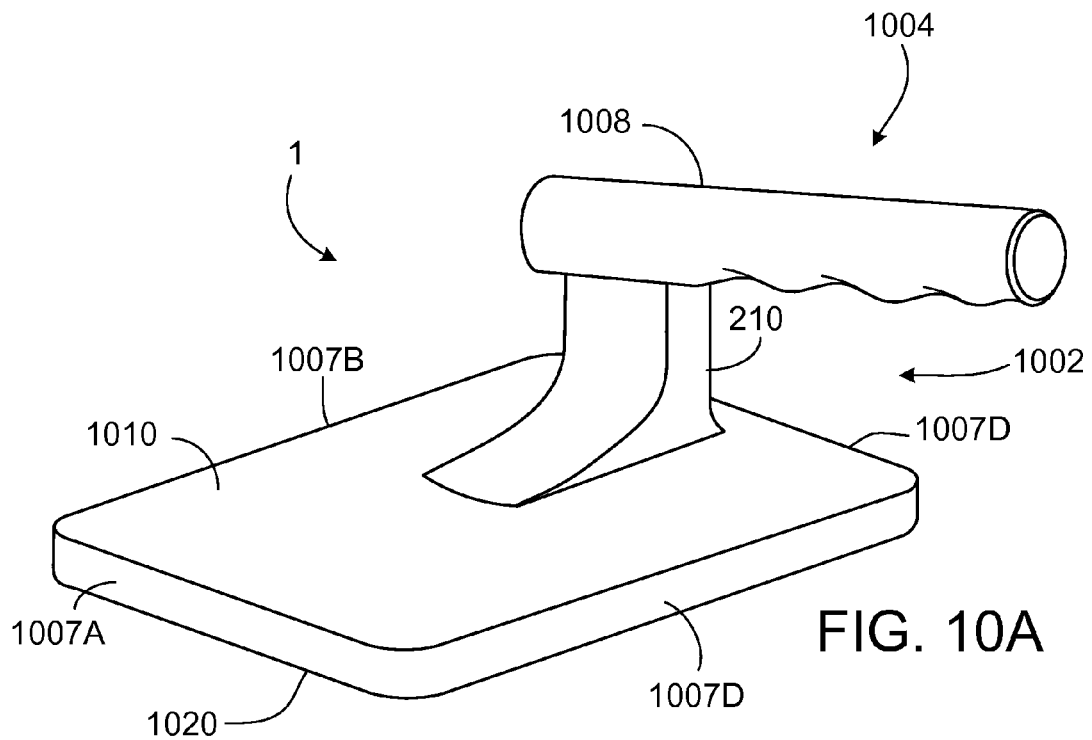
FIG. 10A to 10D depict various implementations of the handheld treatment device of FIG. 1.
Figure 10B:
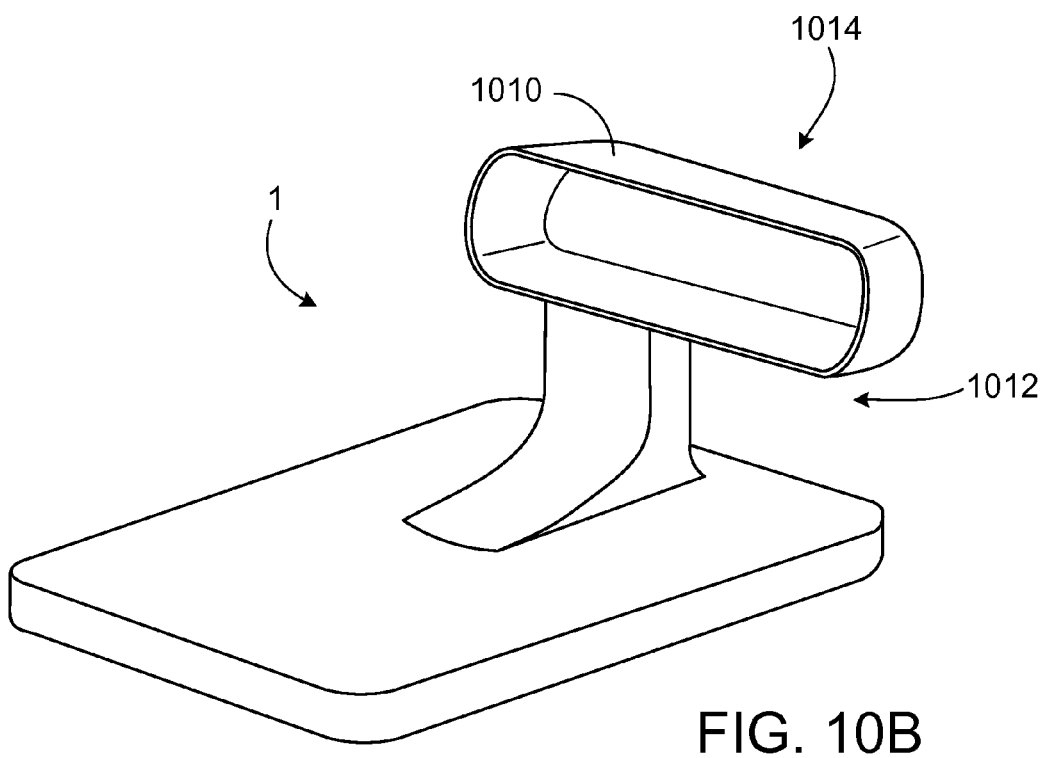
Figure 10C:
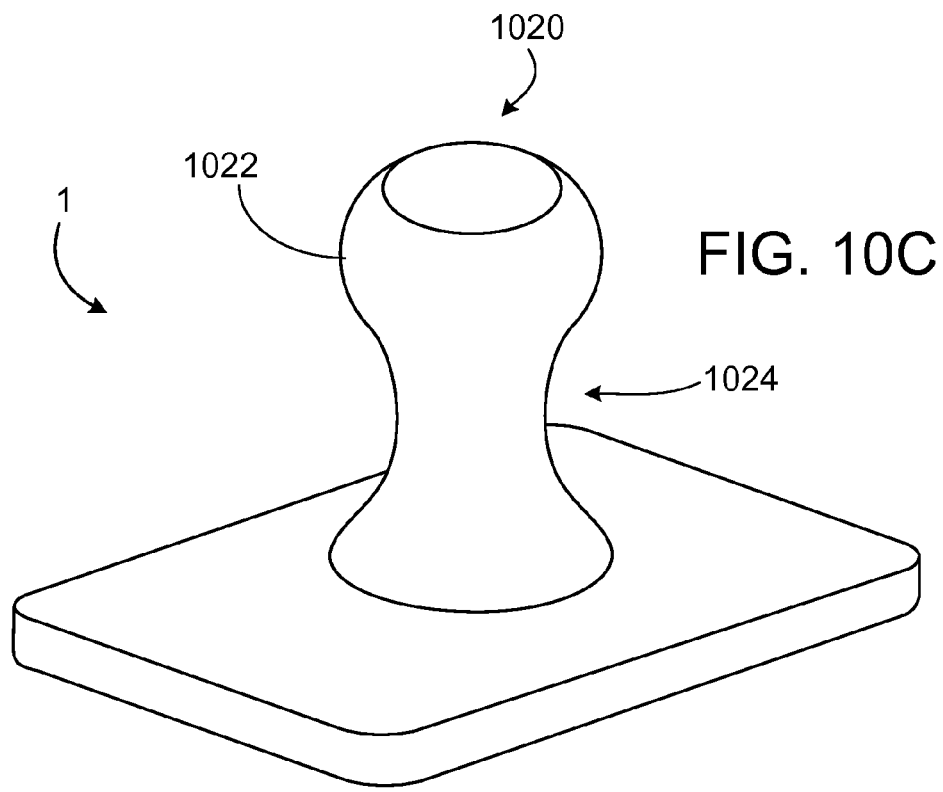
Figure 10D:
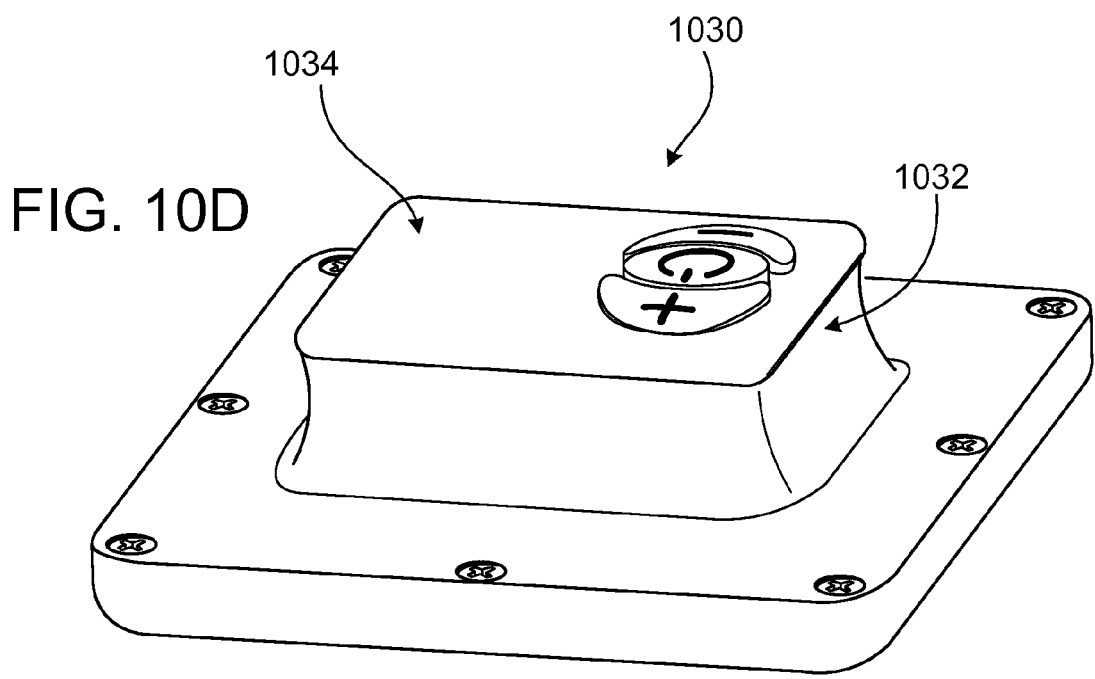

FIGS. 10A-10D each show different implementations of the handheld treatment device 1. Each of FIGS. 10A-10D illustrates a different configuration of the handle member. In FIG. 10A, the handle member 1000 includes a vertical portion 1002 and a horizontal portion 1004. The horizontal portion 1004 is coupled to the vertical portion such that a longitudinal axis of the horizontal portion is parallel to side surfaces 1007A and 1007C, rather than perpendicular to those surfaces. In FIG. 10B, the handle member 1010 includes a vertical portion 1012 and a horizontal portion 1014. The horizontal portion 1014 forms an annular grip by defining a passage 1016 in the horizontal portion 1014. In FIG. 10C, the handle member 1020 is a knob grip that includes a narrow neck 1022 that extends upwards into an enlarged knob portion 1024. The knob grip may be constructed in a number of different shapes. For example, the knob grip can have a flared, generally cylindrical neck with a spherical knob portion, as shown, or can have a neck and knob portion that are generally square or rectangular. As an example, FIG. 10D shows a handle member 1030 with a generally rectangular neck portion 1032 and a generally rectangular knob portion 1034.

Figure 11A:
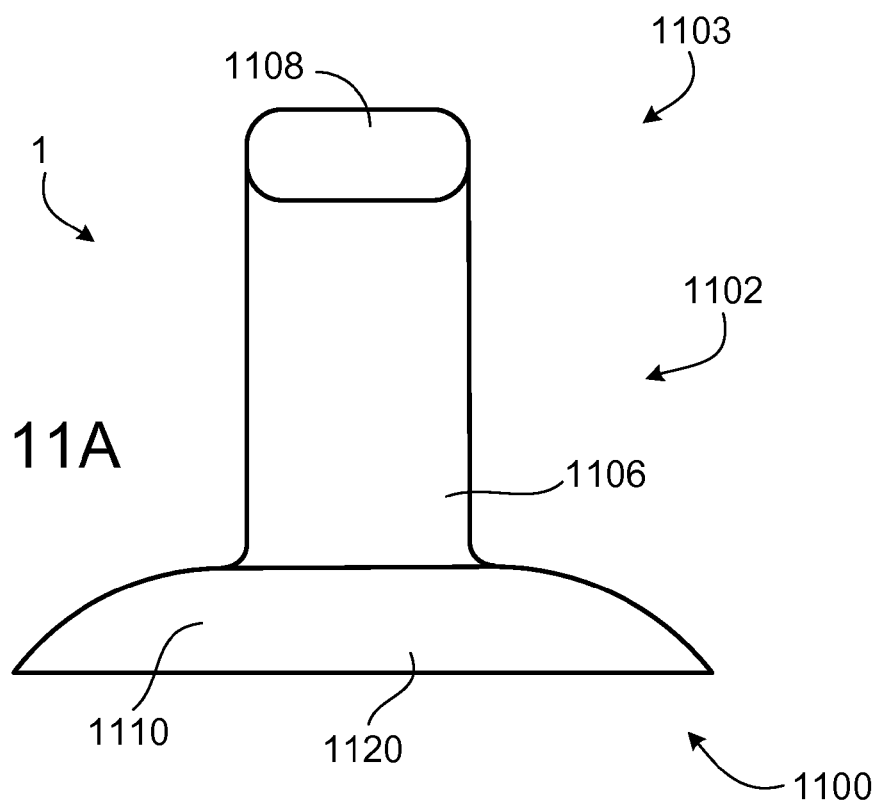
FIGS. 11A to 11B depict various implementations of the handheld treatment device of FIG. 1.
Figure 11B:
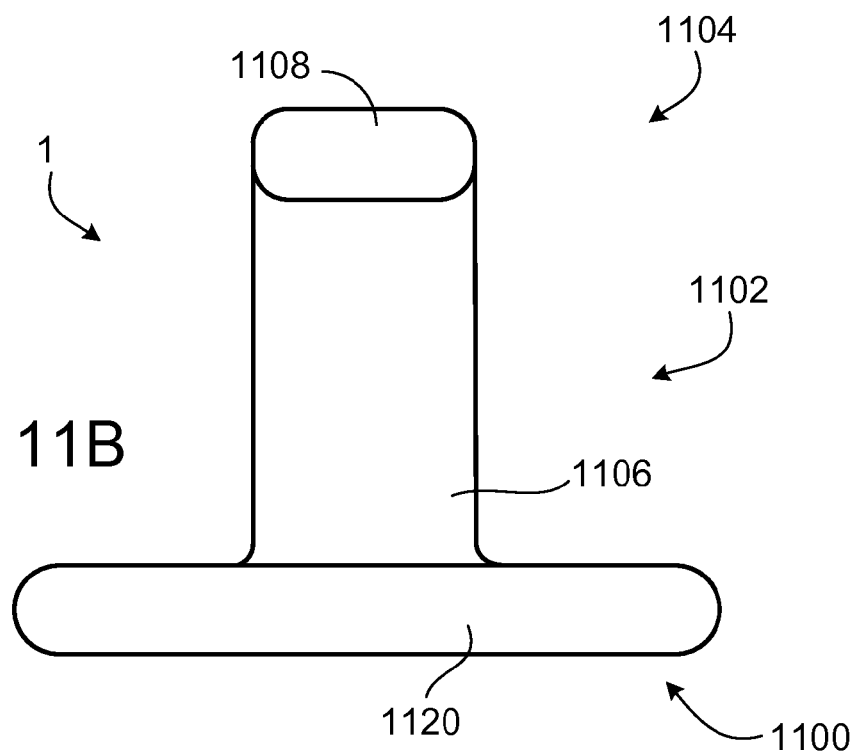

FIGS. 11A-11B shows yet another example of a handheld treatment device that includes a housing with a top portion 1104 and a bottom portion 1100. As shown, bottom portion 1100 can be formed such that top surface 1110 is tapered on the sides and joins bottom surface 1120. In fact, in this example, there are no sidewalls surrounding bottom portion 1100. The top portion 1103 includes a handle member 1108, which in turn, includes a vertical portion 1102 and a horizontal portion 1104.

Figure 12A:
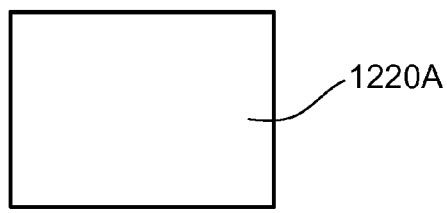
FIGS. 12A to 12D depict various implementations of the handheld treatment device of FIG. 1.
Figure 12B:
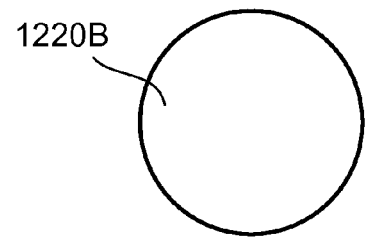
Figure 12C:
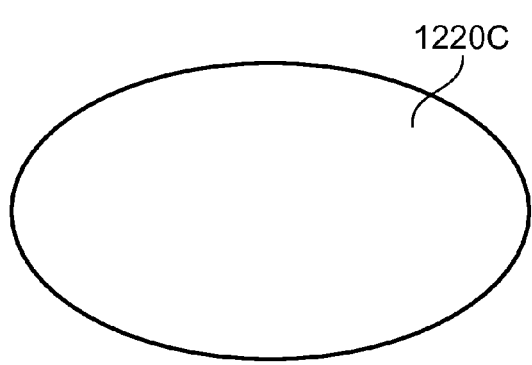
Figure 12D:
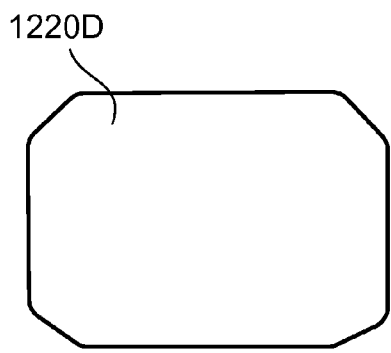

FIGS. 12A-12D further demonstrate various shape configurations of bottom surface of handheld treatment device. For example, bottom surface 1220A may be a rectangular form factor (FIG. 12A). In another example, bottom surface 1220B is a circular form factor (FIG. 12B). In yet another example, bottom surface 1220C is an oval form factor (FIG. 12C). In still another example, bottom surface 1220D is a cropped form factor (FIG. 12D).

The various implementations discussed represent example configurations only. Other implementations are possible. For example, any one of the charging coil, circuit board, and battery, or the combination of all three, may be located in the top portion, for example, in the handle member. The antenna alone may occupy the bottom portion. Some implementations may not stack the circuit board and battery over the charging coil. By way of illustration, while the various parts of the handheld treatment device can be tightened by screws, some implementations may use a latching mechanism to hold the various parts of the handheld treatment device together. Moreover, in some implementations, the various parts of the handheld treatment device can be ultrasonicly welded.

The various implementations of the handheld treatment device described above may have particular advantages. For example, the various implementations may be particularly beneficial because of the compact form. With the provision of the top portion with a handle member and the bottom portion holding functional components, the handheld treatment device may provide both a way for an operator to grip the treatment device as well as the functional components in a small form factor. The antenna cover housing section may contribute to this compact form by allowing multiple layers of electrical components, e.g., control circuitry, antenna, and battery, within the hollow bottom portion.

The various implementations may be particularly beneficial because of their ease of use. By providing a handle member, the handheld treatment device provides an easy way for an operator to handle the device. In some cases, this handle member may provide a convenient underhand grip that is parallel to the contact surface of the bottom portion and thus parallel to the patient's body in many instances. This grip arrangement may provide a comfortable and convenient handling mechanism for an operator of the handheld treatment device.

The various implementations may be particularly beneficial because of their simple design. For example, using the housing arrangement of FIGS. 8A-8E allows for only two external housing members. Furthermore, in some implementations, the cover housing section combines the handle member with the vertical member, while having an opening towards the bottom for easy attachment of the base housing section. Furthermore, in some implementations the hollow portion between the cover housing section and the base housing section is completely open prior to attachment. In these cases, this configuration may allow easy access to the internal portion of the handheld treatment device prior to assembly. As a result, the internal components may be easily positioned, connected, or otherwise arranged prior to attachment of the two external housing portions, which may allow easy manufacture of the components of the device and easy assembly of the components to form the handheld treatment device.

The construction and arrangement of the elements as shown in the exemplary embodiments are illustrative only. Although only a few embodiments of the present disclosure have been described in detail, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements. The elements and assemblies may be constructed from any of a wide variety of materials that provide sufficient strength or durability, in any of a wide variety of colors, textures, and combinations. Additionally, in the subject description, the word "exemplary" is used to mean serving as an example, instance, or illustration. Any embodiment or design described herein as "exemplary" is not necessarily to be construed as preferred or advantageous over other embodiments or designs. Rather, use of the word "exemplary" is intended to present concepts in a concrete manner. Accordingly, all such modifications are intended to be included within the scope of the present disclosure. Other substitutions, modifications, changes, and omissions may be made in the design, operating conditions, and arrangement of the preferred and other exemplary embodiments without departing from the scope of the appended claims.

What is claimed is:

1. A handheld treatment device for facilitating neurophysiological treatment of a patient harboring an implanted neural stimulator, the handheld treatment device comprising:
    a handheld housing comprising a bottom portion connected to a top portion having a handle member adapted for holding by a hand of an operator;
    a transmitting antenna located in the handheld housing and configured to accept one or more input signals and to transmit one or more electromagnetic signals through non-inductive coupling to a passive neural stimulator that is implantable in the patient's body;
    control circuitry located in the handheld housing and configured to provide the one or more input signals to the transmitting antenna;
    a circuit board; and
    a battery;
    wherein the bottom portion of the handheld housing comprises:
        a bottom surface;
        a base housing section segment defining the bottom surface and, on a surface opposite to the bottom surface, defining an antenna recess that provides an indented area on the surface opposite to the bottom surface such that the transmitting antenna is accommodated in the indented area of the antenna recess;
        an antenna cover housing section that is arranged in the base housing section such that a first surface of the antenna cover housing is facing the transmitting antenna in the antenna recess; and
        wherein the antenna housing section includes a second surface, opposite the first surface of the antenna housing section, that includes a holding space in which the circuit board supporting the control circuitry and the battery are located, the antenna housing section providing electrical isolation between the transmitting antenna and holding space for the circuit board and the battery while the one or more electromagnetic signals are being transmitted non-inductively to the passive neural stimulator.

2. The handheld treatment device of claim 1, wherein the transmitting antenna is a patch antenna, a dipole antenna, spiral antenna or other antenna configuration within a form factor of the handheld treatment device.

3. The handheld treatment device of claim 1, further comprising an inductive charging component configured to receive electromagnetic energy wirelessly from outside the handheld treatment device and through inductive coupling, and to recharge the battery mounted in the bottom portion of the handheld treatment device using the received electromagnetic energy, the inductive charging component and the transmitting antenna located on opposite sides of the battery.

4. The handheld treatment device of claim 1, further comprising a control panel with at least one interface button, the control panel located on the handle member.

5. The handheld treatment device of claim 4, wherein the control panel is located on a surface of the top portion of the handheld treatment device.

6. The handheld treatment device of claim 4, further comprising a cable, wherein the control panel is connected to the control circuitry by the cable, and the cable passes through a hollow portion of the top portion of the handheld treatment device.

7. The handheld treatment device of claim 4, wherein a first interface button of the at least one interface button controls at least one neuro stimulation setting of the control circuitry.

8. The handheld treatment device of claim 7, wherein the at least one neural stimulation setting includes at least one of: an amplitude setting, a pulse width setting, a frequency setting, and a preset programs setting.

9. The handheld treatment device of claim 7, wherein a second interface button of the at least one interface button controls which neural stimulation setting of the at least one neural stimulation setting is controlled by the first interface button.

10. The handheld treatment device of claim 1, wherein an elongate portion of the handle member is substantially parallel to the bottom surface of the bottom portion.

11. The handheld device of claim 10, wherein a primary transmission surface of the transmitting antenna is substantially parallel to the bottom surface of the bottom portion.

12. The handheld treatment device of claim 11, wherein the bottom surface of the bottom portion is located between the primary transmission surface of the transmitting antenna and the implanted neural stimulator.

13. The handheld treatment device of claim 1, wherein the battery provides electrical power to at least the control circuitry.

14. The handheld treatment device of claim 13, further comprising at least one charging coil to recharge the battery.

15. The handheld treatment device of claim 14, wherein the recharging coil is configured to receive energy wirelessly from a source external to handheld treatment device and use the energy to recharge the battery.

16. The handheld treatment device of claim 1, wherein the transmitting antenna is configured as a non-loop antenna.

* * * * *